(12) United States Patent
Harrison et al.

(10) Patent No.: US 7,326,774 B2
(45) Date of Patent: Feb. 5, 2008

(54) MONOCLONAL ANTIBODY AND NEMATODE LARVAL ANTIGENS

(75) Inventors: Gavin Bernard Lear Harrison, Kaitoke (NZ); Wayne Robert Hein, Wellington (NZ); Hugh Douglas Pulford, Wellington (NZ); Charles Bix Shoemaker, North Grafton, MA (US)

(73) Assignee: Ovita Limited, Wellington (NZ)

( * ) Notice: Subject to any disclaimer, the term of this patent is extended or adjusted under 35 U.S.C. 154(b) by 310 days.

(21) Appl. No.: 10/503,456

(22) PCT Filed: Jan. 30, 2003

(86) PCT No.: PCT/NZ03/00010

§ 371 (c)(1),
(2), (4) Date: Apr. 13, 2005

(87) PCT Pub. No.: WO03/064475

PCT Pub. Date: Aug. 7, 2003

(65) Prior Publication Data

US 2005/0180978 A1    Aug. 18, 2005

(30) Foreign Application Priority Data

Jan. 30, 2002   (AU) ................... PS 0214

(51) Int. Cl.
*A61K 39/395* (2006.01)
*C07K 1/00* (2006.01)
*C07K 16/00* (2006.01)
*G01N 33/53* (2006.01)

(52) U.S. Cl. ............. 530/388.1; 530/350; 530/387.1; 424/130.1; 435/7.1

(58) Field of Classification Search ........... 530/350, 530/387.1, 388.1; 435/7.1; 424/130.1
See application file for complete search history.

(56) References Cited

U.S. PATENT DOCUMENTS

2007/0009981 A1* 1/2007 Williams et al. .............. 435/23

FOREIGN PATENT DOCUMENTS

WO   WO 90/03433 A1   4/1992
WO   WO 92/13890 A1   8/1992

OTHER PUBLICATIONS

Plotkin et al (Vaccines WB Saunders Company 1988, p. 571).*
Jasmer et al (Journal of Immunology vol. 151, No. 10, pp. 5450-5460, Nov. 1993).*
Harrison G.B.L. et al., "Characterization of a 35-kDa Carbohydrate Larval Antigen Colubriformis; A Potential Target for Host Immunity", Parasite Immunology (Oxford), vol. 25, No. 2, Feb. 2003 pp. 79-86, XP002350701 ISSN:0141-9838.
Harrison G.B.L. et al. "Immune Rejection of Trichostrongylus Colubriformis In Sheep: a Possible Role for Intestinal Mucus Antibody Against an L3-specific Surface Antigen." Parasite Immunology (Oxford), vol. 25, No. 1, Jan. 2003, pp. 45-53, XP002350702 ISSN: 0141-9838.
H.J. Jacobs et al. 'Vaccination against the gastrointestinal nematode, *Haemonchus contortus*, using a purified larval surface antigen.' Vaccine, 1999, vol. 17, pp. 362-366.
J. Charley-Poulain et al. 'Serum and Abomasal Antibody Response of Sheep to Infections in *Haemonchus Contortus*.' Veterinary Parasitology, 1984, vol. 14, pp. 129-141.

* cited by examiner

*Primary Examiner*—Mark Navarro
(74) *Attorney, Agent, or Firm*—Knobbe, Martens, Olson & Bear, LLP

(57) ABSTRACT

The present invention relates to an isolated monoclonal antibody mAb PAB-1, deposited at ATCC on 24 Jan. 2002 and accorded accession PTA-4005, which binds to a surface antigen on nematode L3. It also relates to the antigen which binds to the monoclonal antibody and uses for the monoclonal antibody and antigen in diagnosing and treating or preventing nematode infection.

17 Claims, 32 Drawing Sheets

FIGURE 1. Numbers of larvae establishing in naïve sheep after incubation with 5 or 10 ml mucus from naïve sheep (hatched) or 2.5, 5, 7.5 or 10 ml mucus from immune sheep (black).
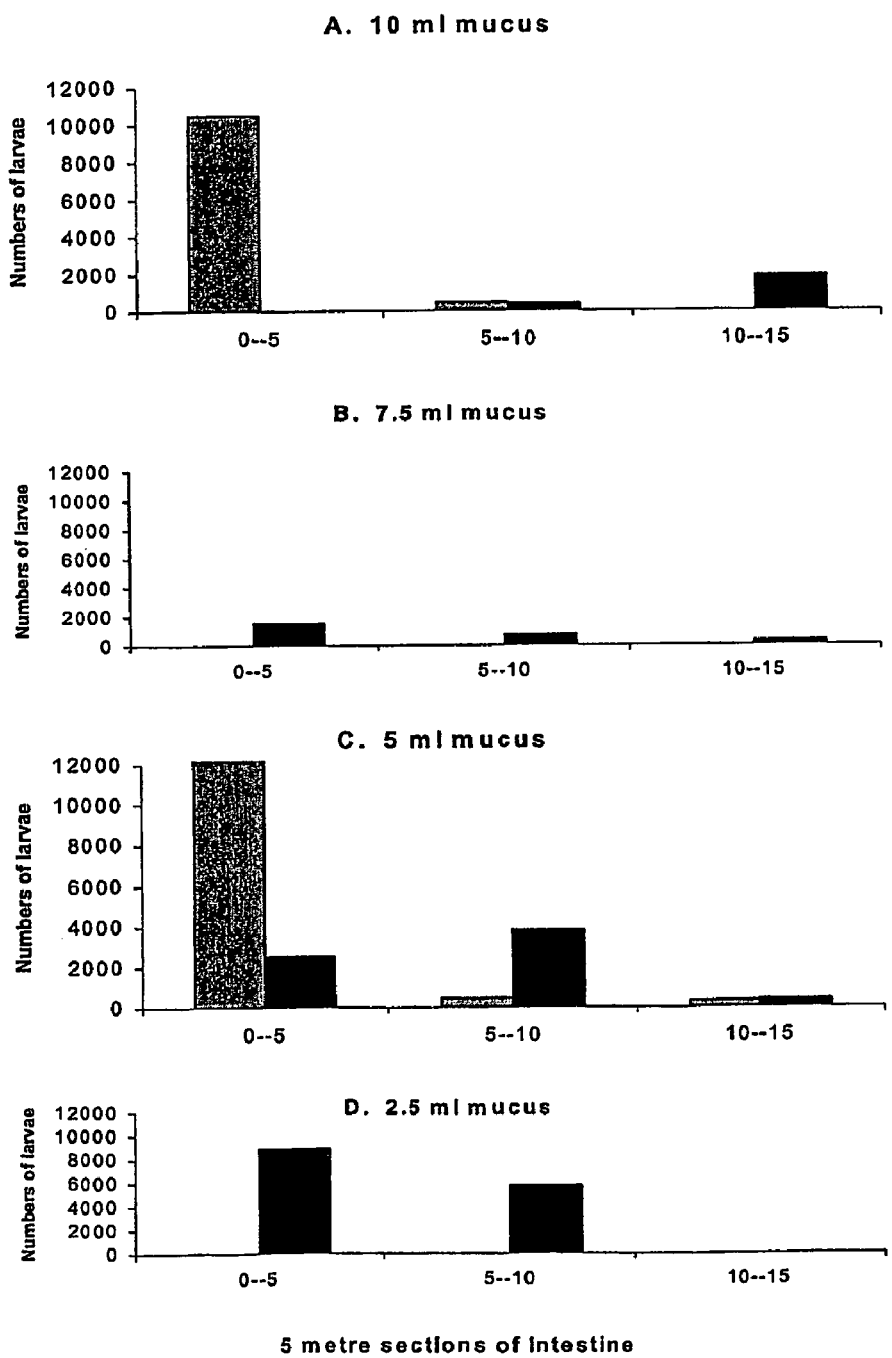

FIGURE.2  Numbers of larvae in naive sheep after incubation with mucus from naive sheep (hatched) or immune sheep (black) for various times.
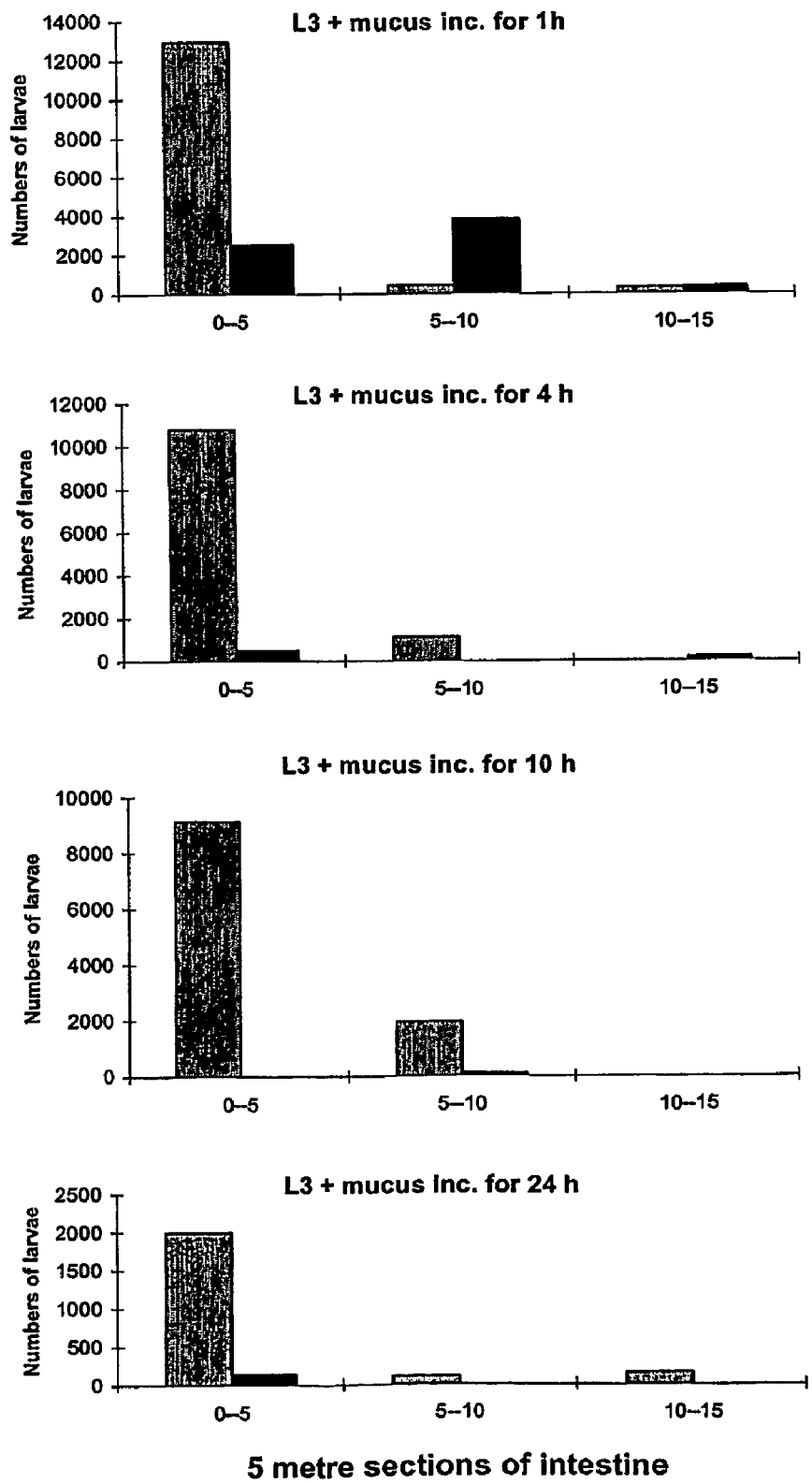
5 metre sections of intestine

FIGURE 3. Numbers of larvae in the proximal 5m of intestine compared to numbers of larvae in the distal 10m of intestine of naïve recipient sheep infused with mixtures of L3 with naïve mucus (top panel) or immune mucus.
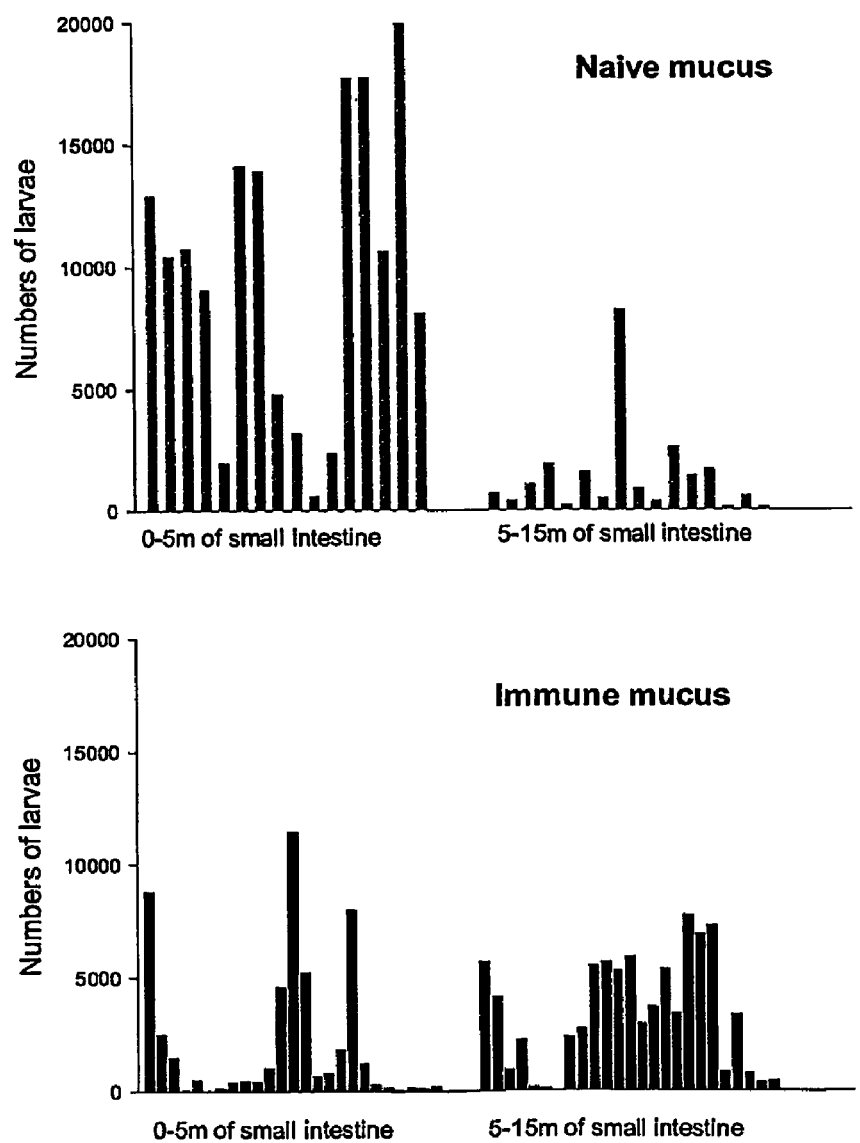

FIGURE 4. Anti-larval activity of immune mucus relative to time of collection after immuisation.
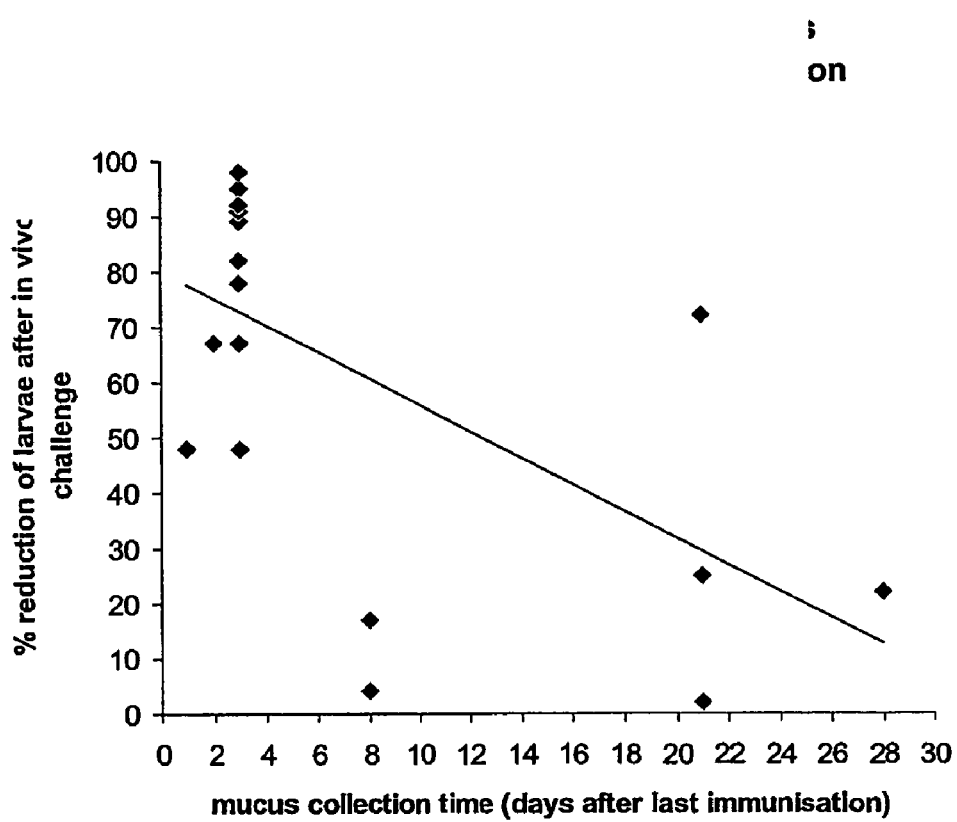

FIGURE 5. SDS PAGE analysis of mucus samples from naive sheep or from sheep immunised by truncated infection with *T. colubriformis*. Top panel, samples stained with Coomassie blue; bottom panel, samples stained with silver.
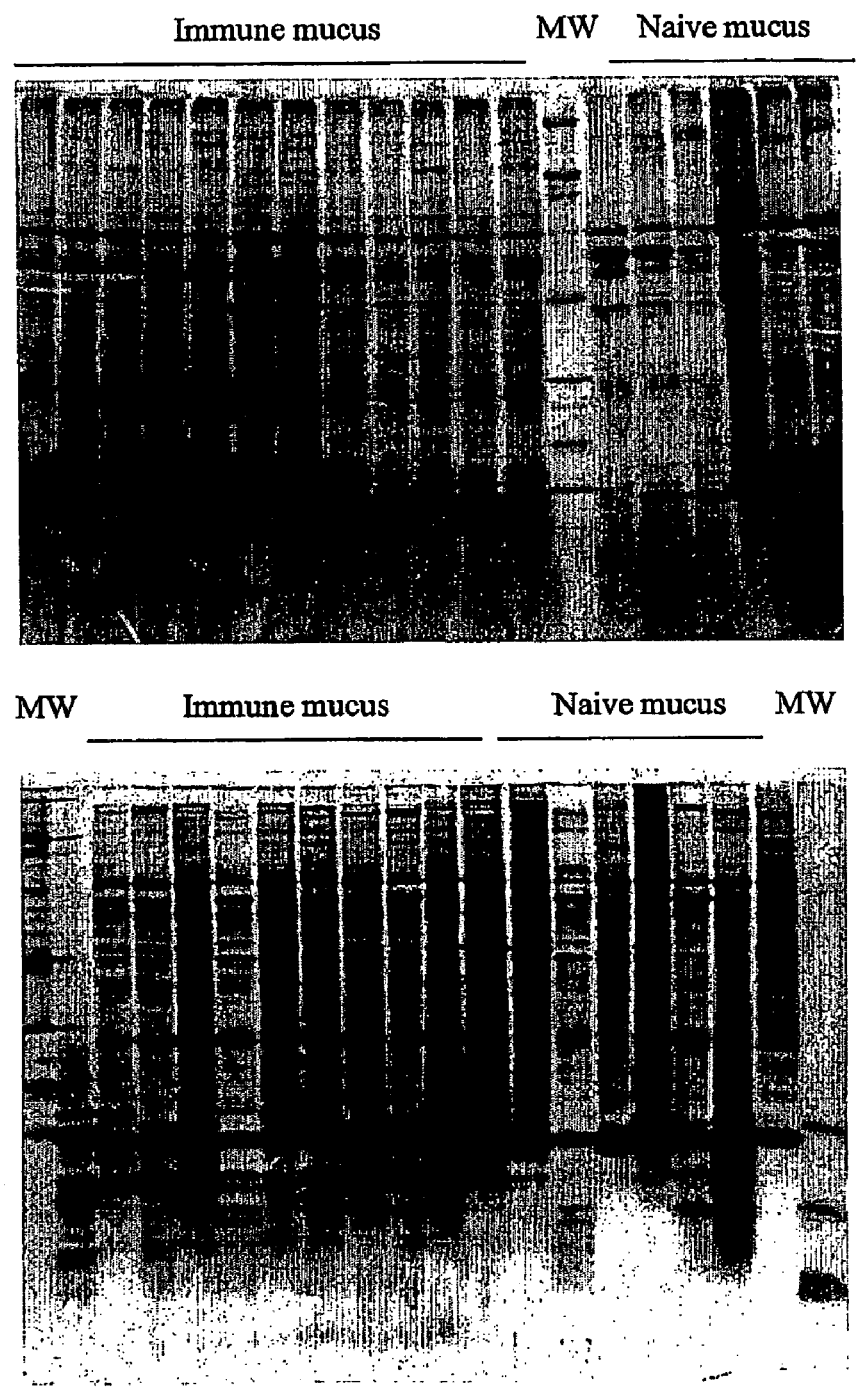

FIGURE 6. Lectin blotting of immune mucus (left half of each panel) and naïve mucs. A; UEA-1 (α-L-fucose). B; JAC (α-gal-Me-pyranoside). C; WGA (N-acetylglucosamine). D; LL (mannose, glucose).
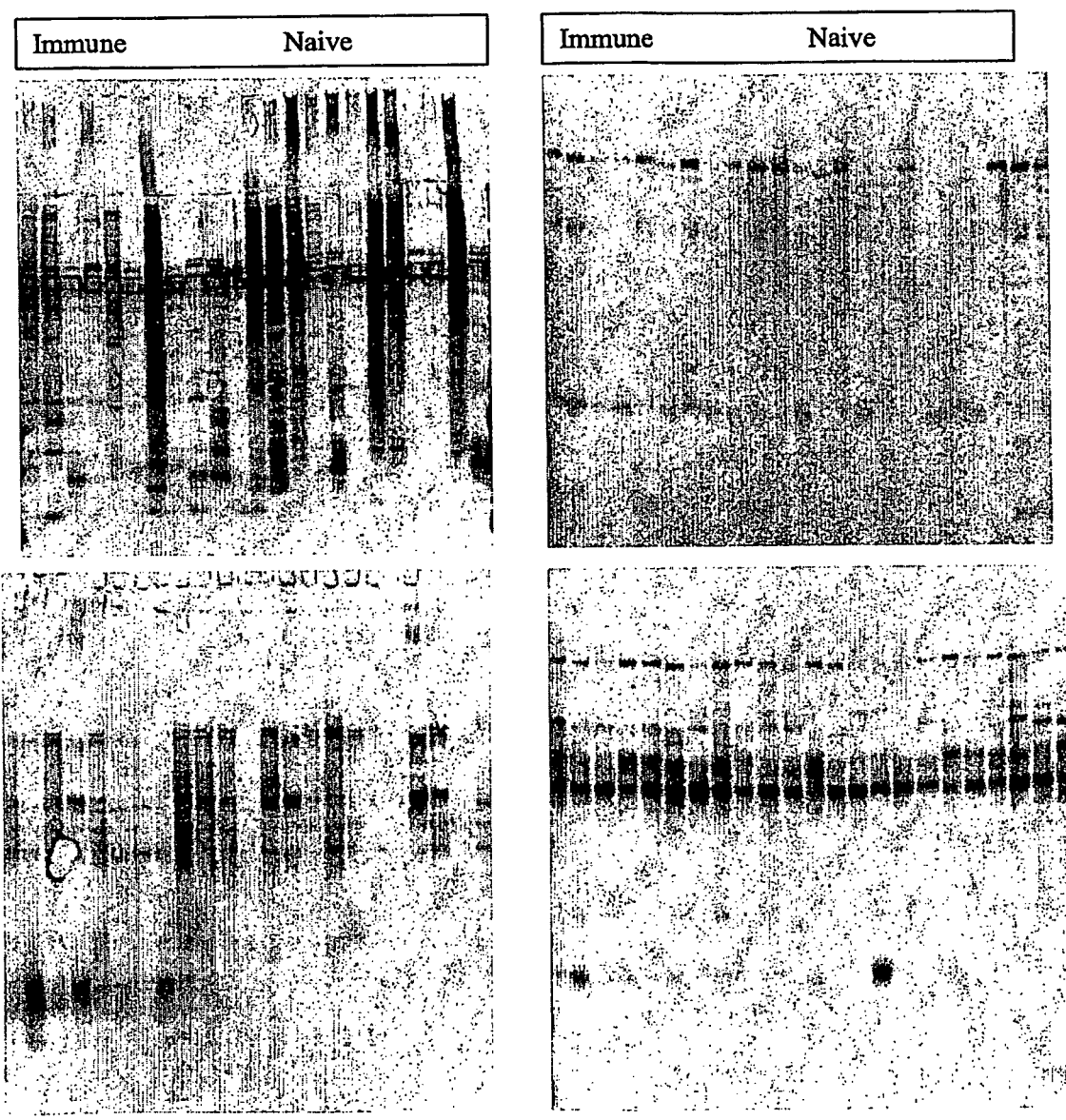

FIGURE 7. Lectin blotting of immune mucus (left half of each panel) and naive mucus.
A; PNA (β-galactose-N-acetylgalactosamine). B; EcorA (β-galactose-N-acetylglucosamine).
C; SBA (N-acetylgalactosamine). D; ECA (β-galactose-N-acetylglucosamine).
Arrows indicate 70 and 28 kDa.
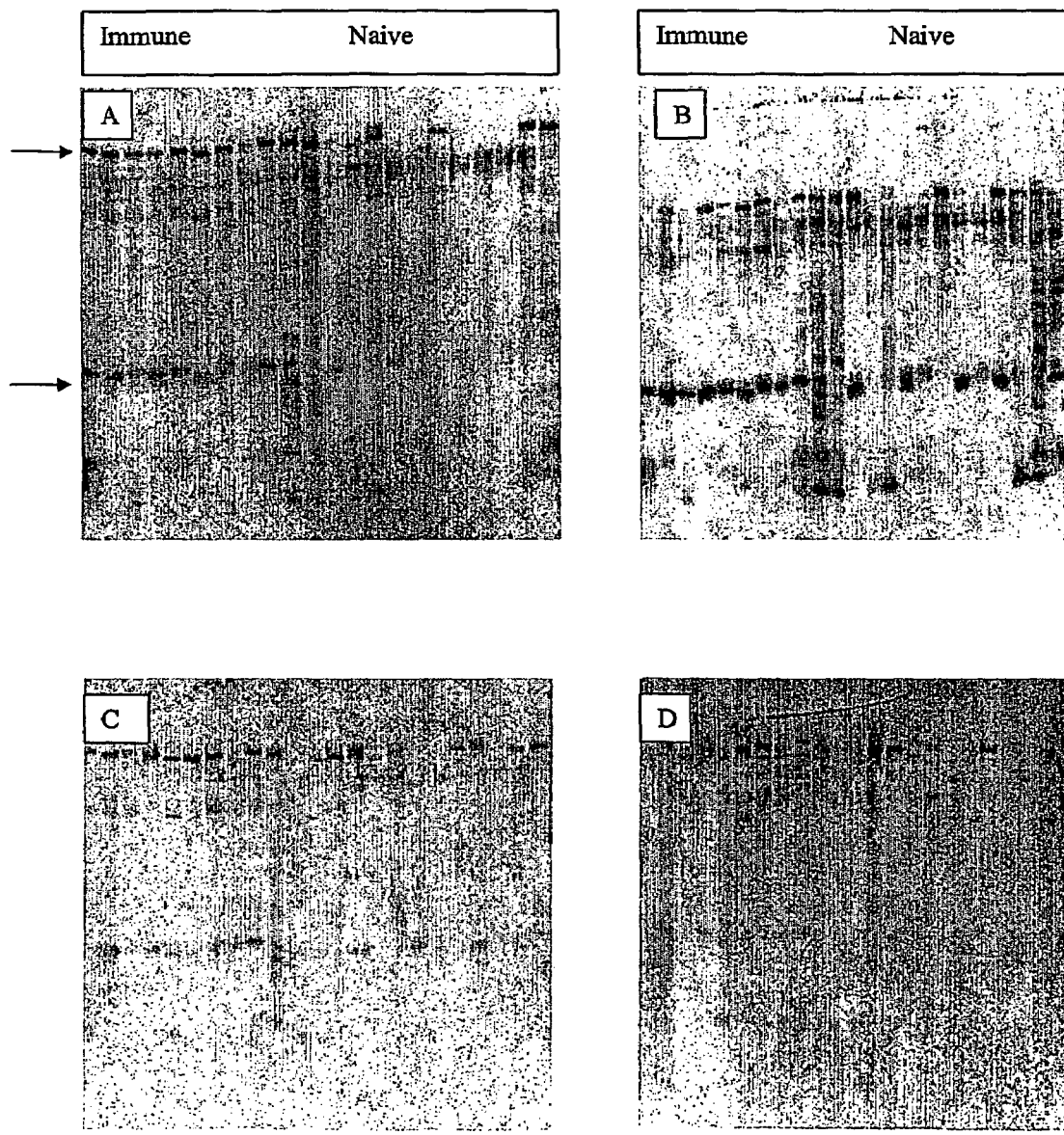

FIGURE 8. Lectin blotting of immune mucus (left half of each panel) and naive mucus. A; SNA (sialic acid).
B; immunoblot probed with RAS/IgG-HRP.
Arrows indicate 55 and 27 kDa.
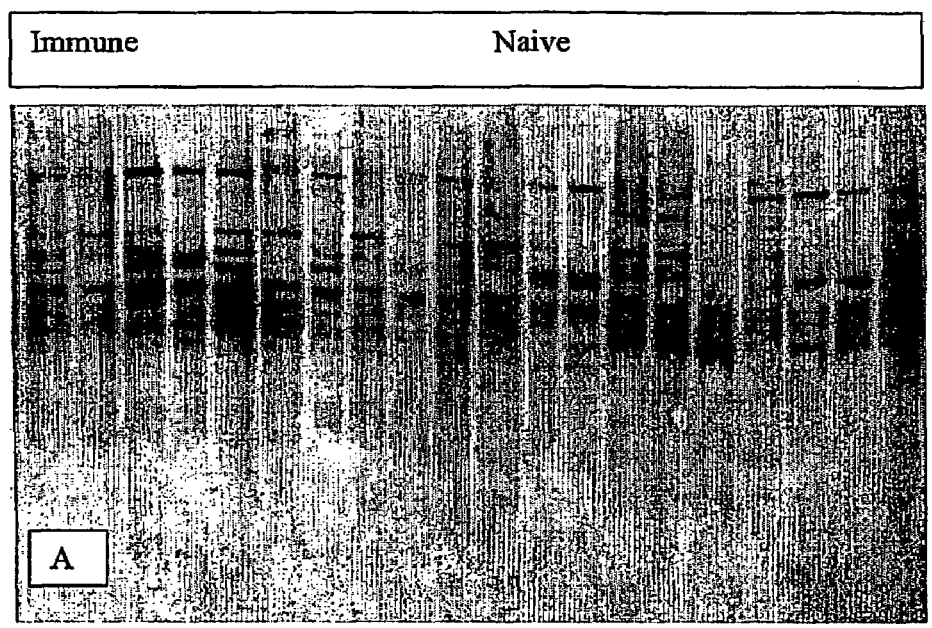
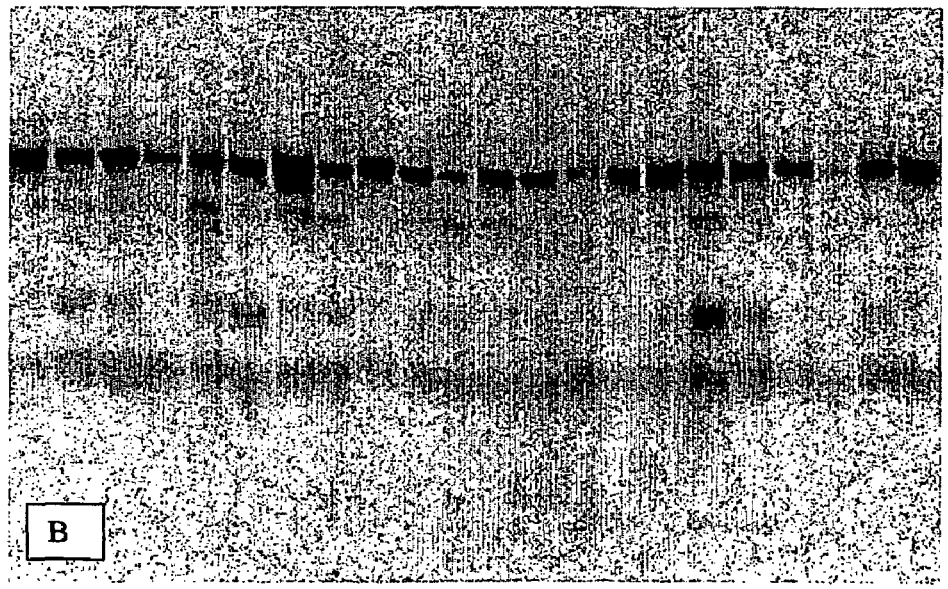

FIGURE 9. Immunoblot of Tc L3 antigen probed with intestinal mucus from immune sheep (lanes 1, 5, 10, 11, 12 and 19) or naïve sheep (lanes 13-18), 100 000 x g supernatant of immune mucus (lane 3), immune mucus supernatant purified from Protein G-agarose (lanes 4 and 7), antibody eluted from exsheathed Tc L3 (lanes 6 and 20), antibody from ammonium sulphate precipitated gut lumen fluids from two immune sheep (lanes 8 and 9). Lane 2 shows Tc L3 proteins stained with colloidal gold. IgG antibody was detected with RAS/IgG-HRP (lanes 1-18) and IgA was detected with MAS/IgA followed by RAM/IgG-HRP (lanes 19 and 20).

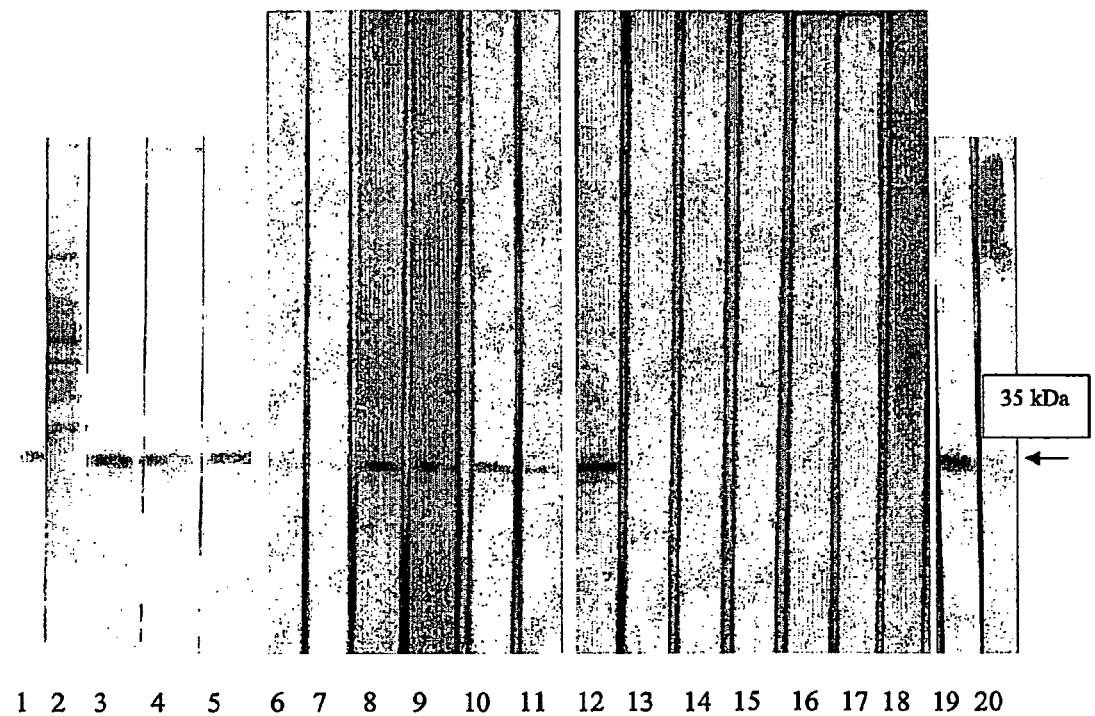

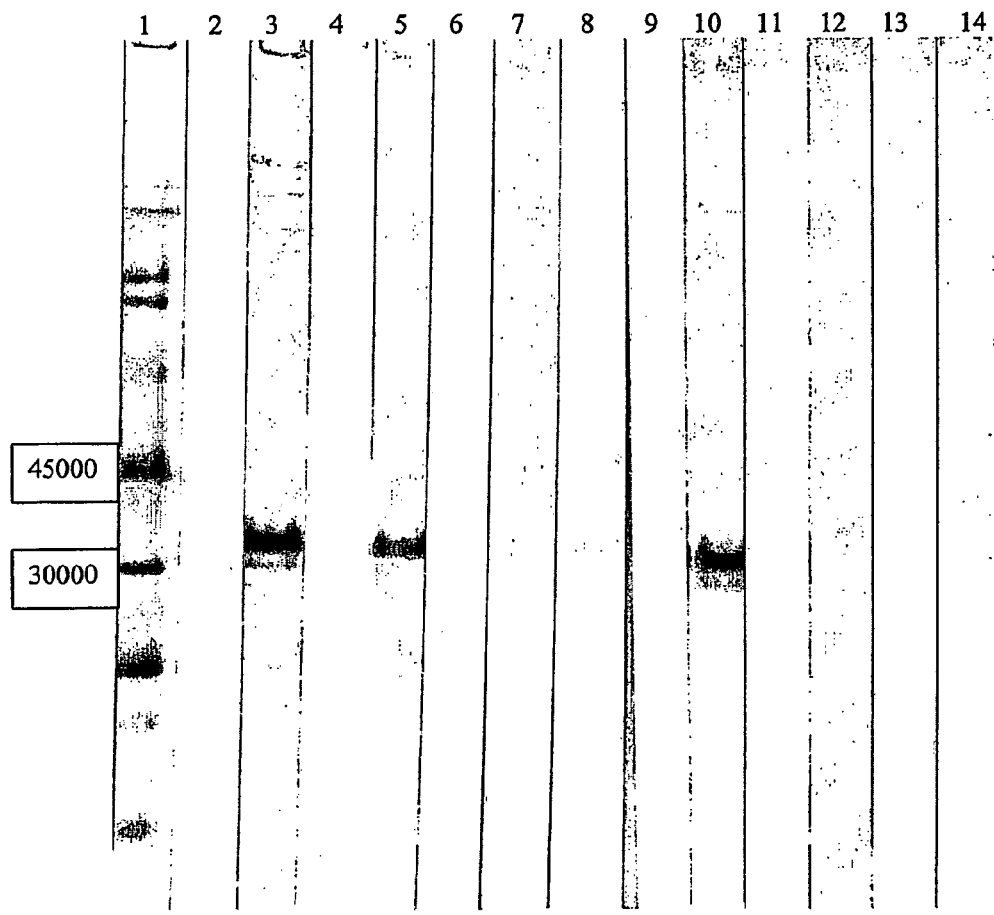
FIGURE. 10 Immunoblot of Tc L3 antigen probed with naive or immune mucus. Antigen strips were reacted with naive mucus (lanes 2,4,6,9,11,13) or immune mucus (lanes 3,5,7,10,12,14) followed by RAS/IgG (lanes 2 & 3); mAb to sheep $IgG_1$(lanes 4 & 5); mAb to sheep $IgG_2$ (lanes 6 & 7); mAb to sheep IgA (lanes 9 & 10); mAb to sheep IgM (lanes 11-14).
Lane 1, Pharmacia MW markers. Lane 8, Bio Rad prestained MW markers.

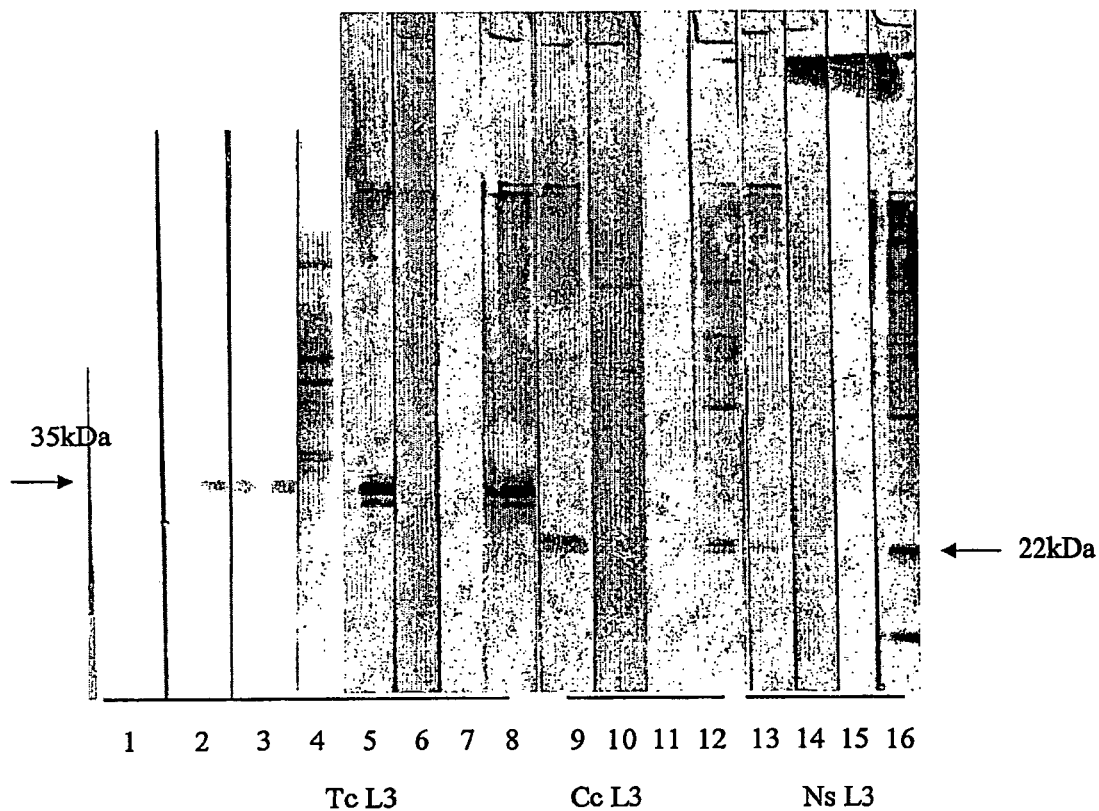

FIGURE 11. Immunoblot of Tc L3 antigen (lanes 1-8), Cc L3 antigen (lanes 9-12) and Ns L3 antigen (lanes 13-16) probed with mucus from Tc immune sheep (lanes 2, 3, 5, 9, 13); mucus from Ns immune sheep (lanes 6,10, 14); ammonium sulphate precipitate of gut contents from Ns immune sheep (lanes 7, 11, 15); sera from Ns immune sheep (lanes 8, 12, 16). Lane 1 probed with mucus from Tc immune sheep after absortion with 260 000 exsheathed Tc L3. Lane 4, Tc L3 antigen stained with colloidal gold protein stain. Arrows indicate position of 35 or 22 kDa antigens. Antibody detected with AS/IgG-HRP.

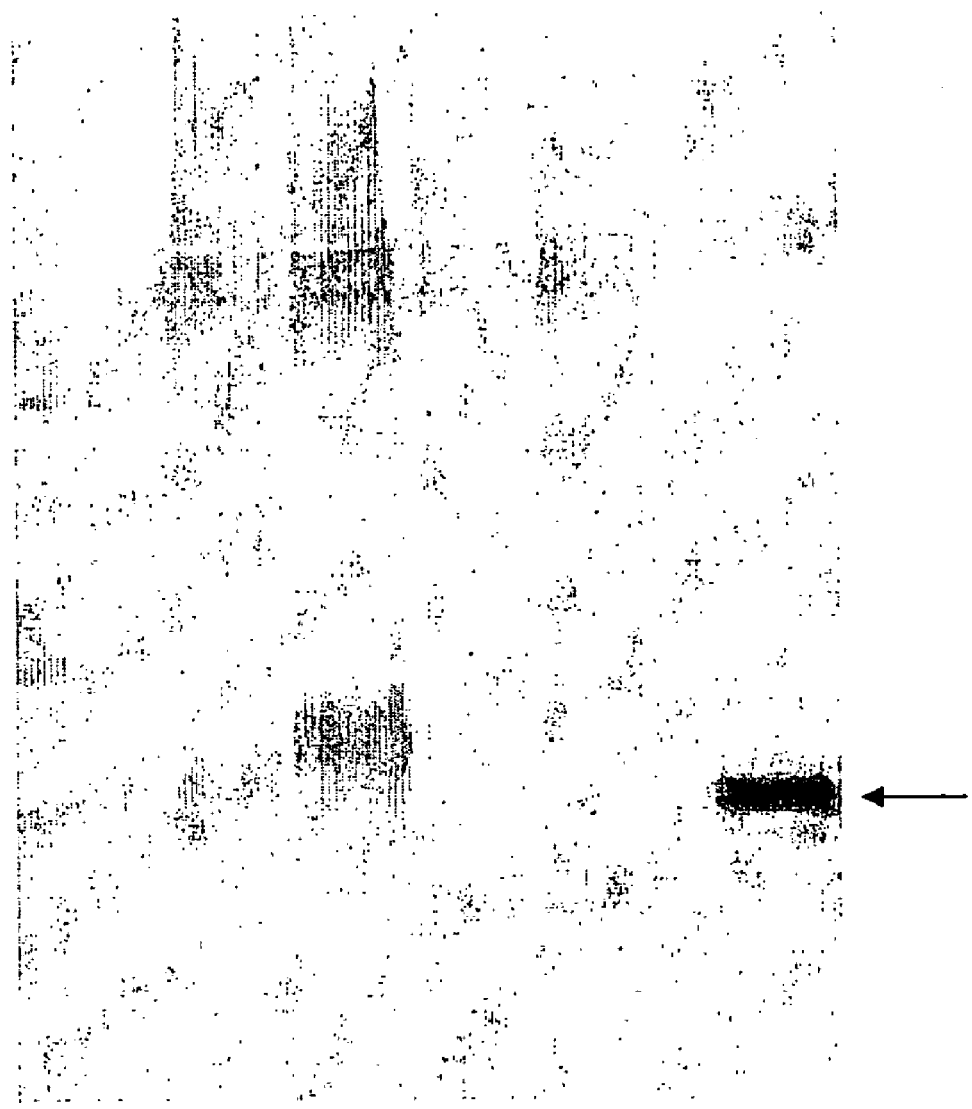
FIGURE 12. Immunoblot analysis of extracts from L3 of;
Lane 1. *H. contorts*
Lane 2. *O. circumcincta*
Lane 3. *N. spathiger*
Lane 4. *C. curticei*
Lane 5. *T. colubriformis*
Blot was probed with mucus from Tc immune sheep followed by RAS/IgG-HRP. Arrow shows position of 35 kDa antigen.

FIGURE 13. Correlation of intestinal mucus IgG and IgA antibody titre against Tc L3 antigen with protection against challenge infection ( % reduction of larval count compared to controls).
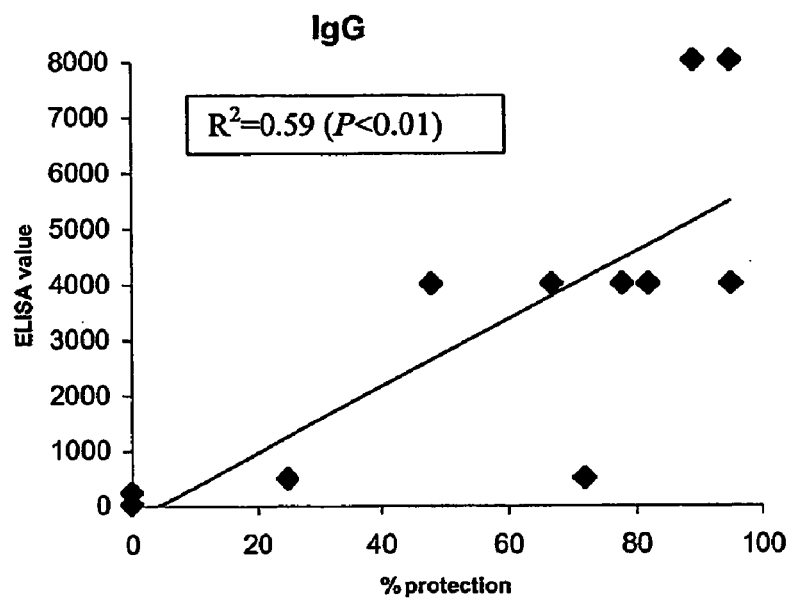
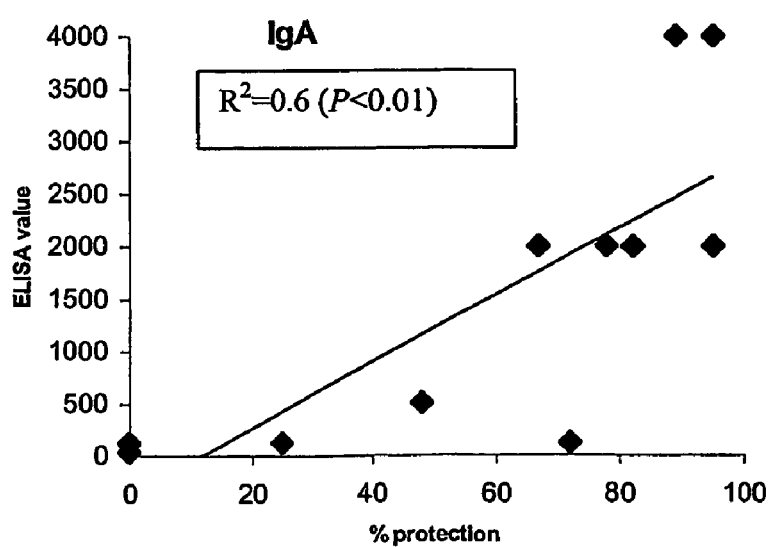

FIGURE 14. IgG and IgA antibody titres in mucus samples taken at biopsy of truncated infection sheep at 3, 16 and 37 days after the sheep were given booster doses of L3.
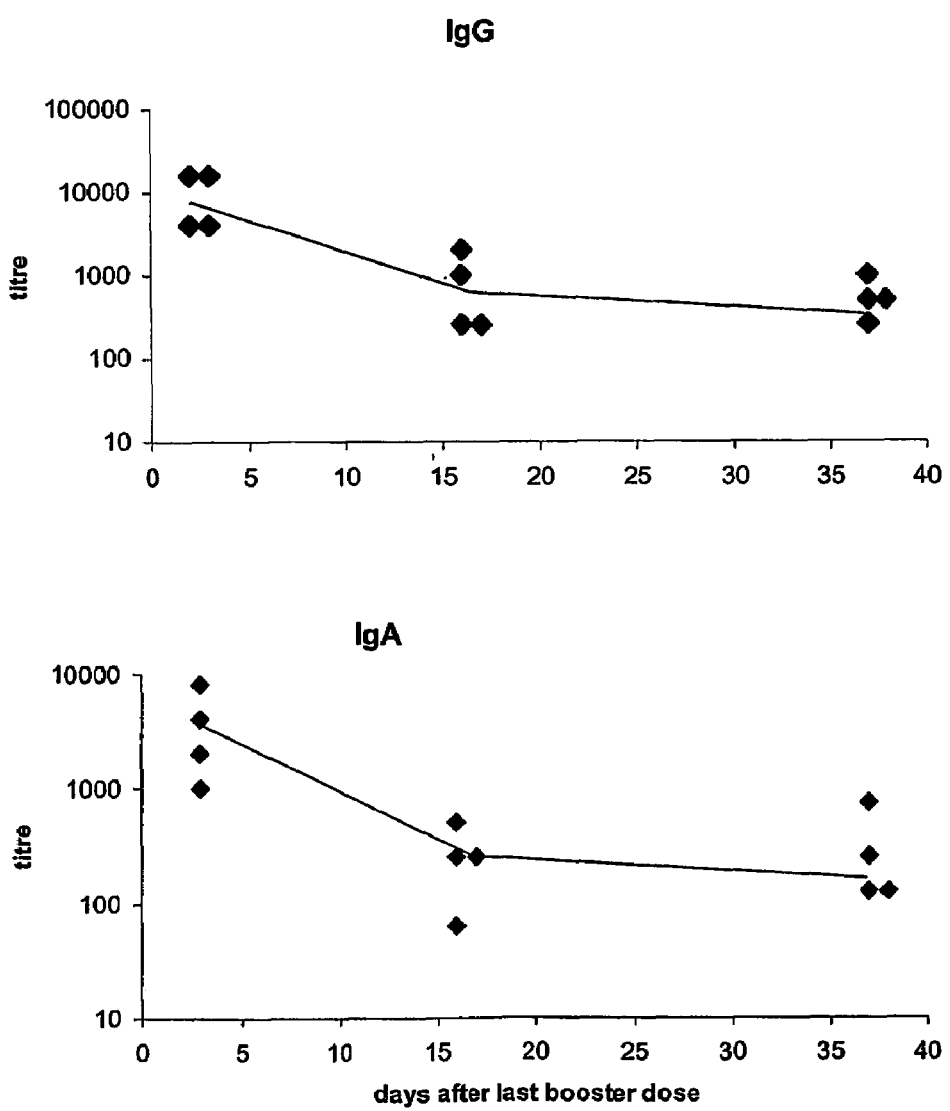

FIGURE 15. Top panels; exsheathed Tc L3 reacted with immune mucus (left) or naïve mucus (right) followed by RAS/IgG-FITC.
Lower panels; Tc larvae collected 5 days after infection and reacted with immune mucus followed by RAS/IgG-FITC. Left slide viewed under uv light; right photo is the same slide viewed under white light.

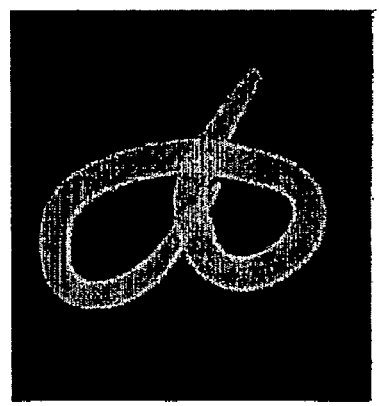 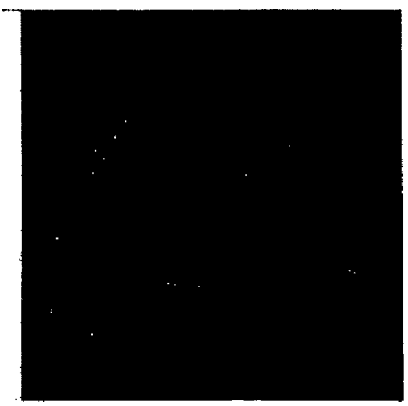

L3 + immune mucus          L3 + naïve mucus

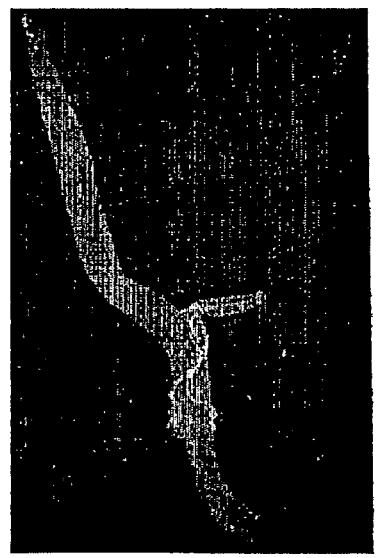 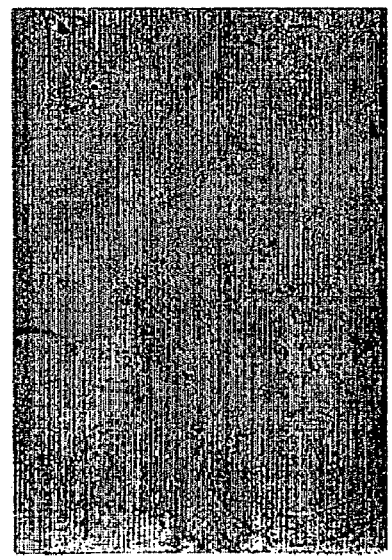

Day 5 larva + immune mucus

FIGURE 16. Electronmicrographs of exsheathed Tc L3 after reaction with naïve mucus (A) or immune mucus (B) followed by RAS/IgG-gold. Panels C,D,E,F are Tc larvae collected at 2,3,4 or 5 days after infection and reacted with immune mucus followed by RAS/IgG-gold. Arrows show surface location of gold labelling.

FIGURE 17. SDS PAGE and immunoblotting analysis of extracts of *T. colubriformis* eggs, larvae and adults. Panels A, C and D reacted with immune mucus; panel B silver stained proteins. Panels A and B: lane 1, Tc eggs; lanes 2,3,4, larvae from day 1,3 and 7 *in vitro*; lane 5, eggs; lanes 6-14, larvae from day 1-9 *in vitro*. Panel C: lane 1, eggs; lanes 2,3,4, larvae from day 1,3,5 *in vitro*; lane 5, L3 after 6 months at 8°C; lane 6, L4 (14 days after infection); lanes 7-9, adults. Panel D: lanes 1& 2, exsheathed L3; lanes 3 & 5, sheaths; lanes 6 &7, L4 (14 days after infection); lanes 8-13, adults.

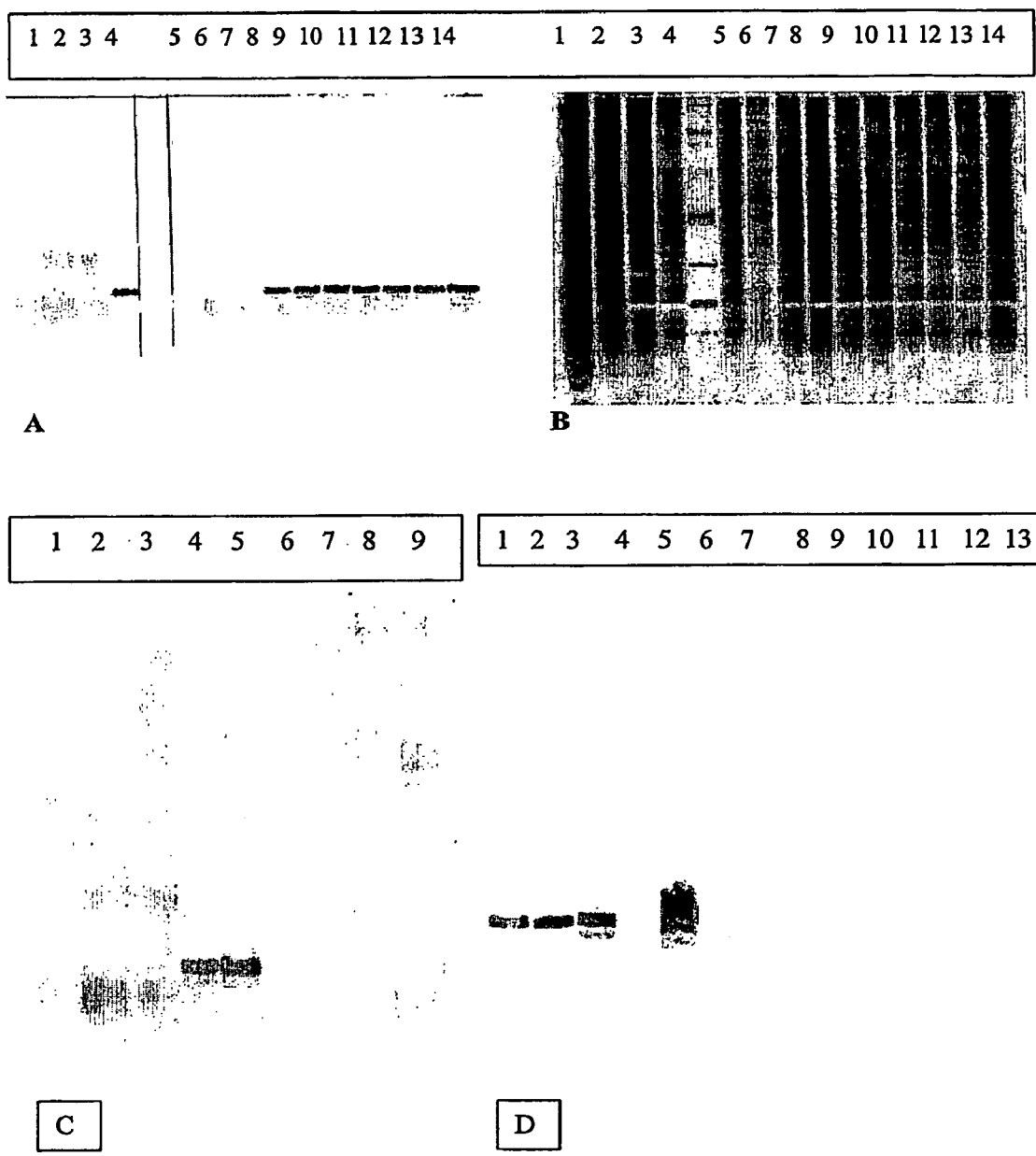

FIGURE 18. SDS PAGE and immunoblotting analysis of *T. colubriformis* L3 before infection and larvae collected at various times after infection. Panel A: lanes 1 & 7, larvae from day 1; lanes 2 & 8, larvae from day 2; lanes 3 & 9, larvae from day 3; lanes 4 & 10, larvae from day 4; lanes 5 & 11, larvae from day 5; lanes 6 & 12, larvae from day 14.

Panel B: lanes 1 & 5, L3 before infection; lanes 2 & 6, larvae from day 5; lanes 3 & 7, larvae from day 6; lanes 4 & 8, larvae from day 7 after infection.

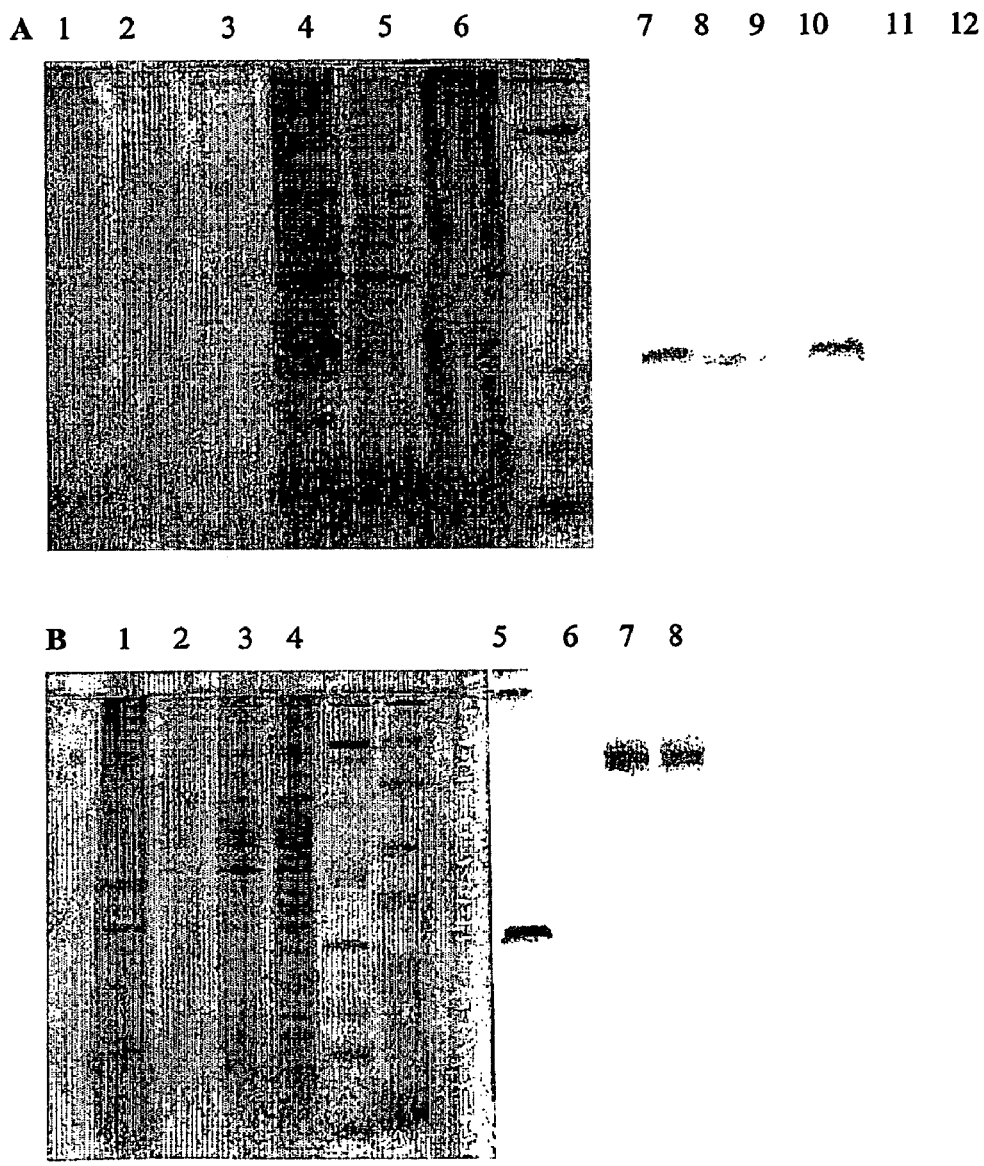

FIGURE 19. Immunoblot analysis of proteinase K digested Tc L3 extracts (lanes 1-4) and Tc L3 extracts (lanes 5 & 6) probed with mAb PAB-1 (A) or immune sheep mucus (B). Antibody was detected with RAM/IgG-HRP (A) or with RAS/IgG-HRP.
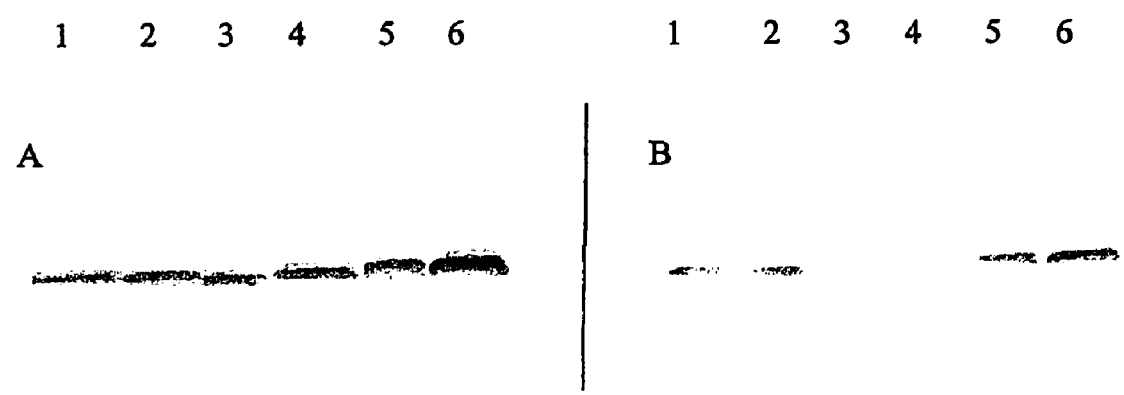

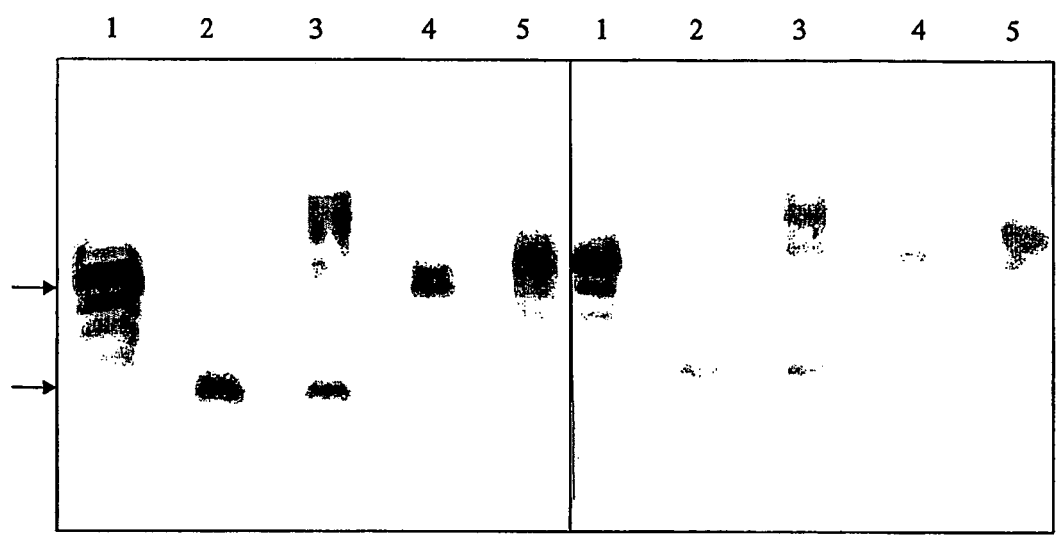
FIGURE 20. Immunoblot analysis of nematode L3 extracts (left panel) or proteinase K digested L3 extracts (right panel) probed with mAb PAB-1 followed by RAM/IgG-HRP. Arrows are at 35 and 22 kDa.
Lane 1. *T. colubriformis*
Lane 2. *N. spathiger*
Lane 3. *C. curticei*
Lane 4. *H. contortus*
Lane 5. *O. circumcincta*

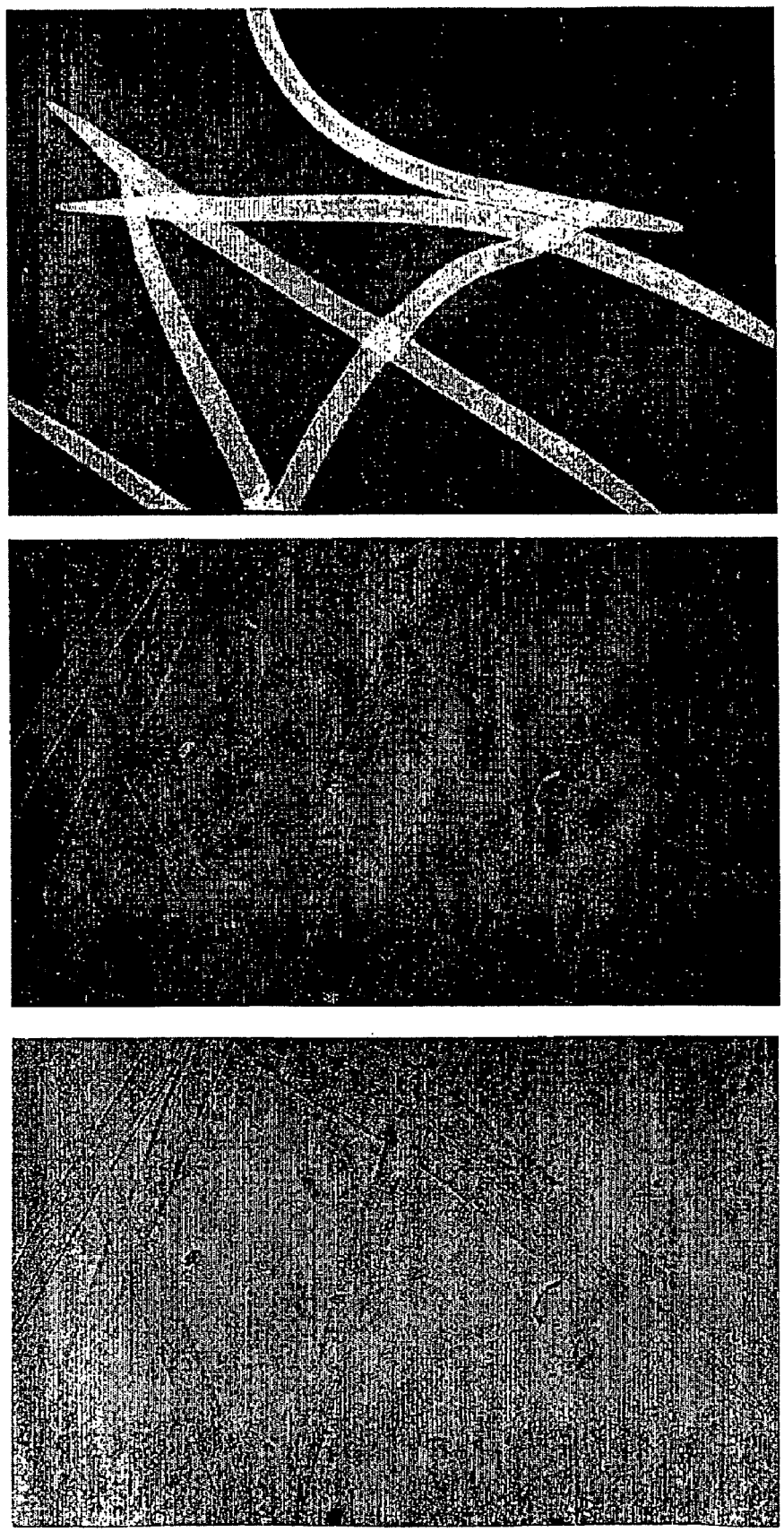
FIGURE 21. Immunofluorescent staining of Tc L3 with monoclonal antibodies. Left and centre panels reacted with control monoclonal antibody PG-G8-D10-E6 (an IgG3 subclass antibody against ovine IL-4). Left panel viewed under white light; centre panel same slide viewed under uv light. Right panel reacted with monoclonal antibody PAB-1. Both slides reacted with RAM/IgG-FITC.

FIGURE 22. Analysis of Tc larval surface antigen purified by immuno-affinity chromatography using mAb PAB-1 coupled to Protein G-agarose. Lanes 1 & 2, antigen eluted from mAb column silver stained for protein or carbohydrate (lanes 3 & 4). Lanes 5-8, antigen eluted from mAb column probed with antibody from immune sheep mucus. Lanes 9 & 12, Tc L3 extract silver stained for protein (9) or carbohydrate (12). Lanes 10 & 11, gel extract of antigen eluted from mAb column silver stained for protein (10) or carbohydrate (11). Lanes 13 & 15, Tc L3 extract labelled in situ with biotin-hydrazide. Lane 14, gel extract of antigen eluted from mAb column labelled in situ with biotin-hydrazide. Arrows show position of Ig heavy and light chains or 35 kDa surface antigen.

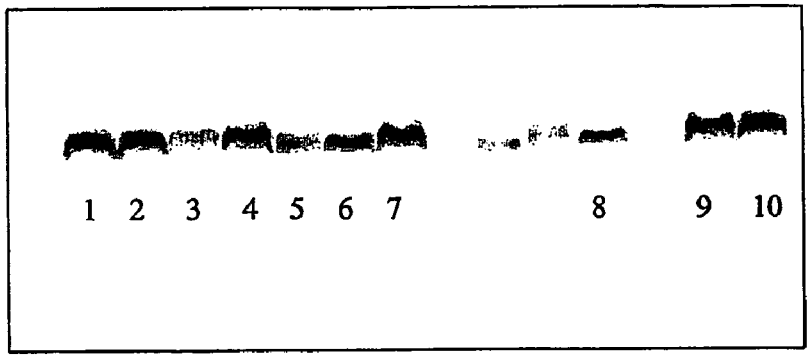

FIGURE 23. Immunoblot of Tc L3 antigen subjected to various treatments: lane 1, untreated control; lanes 2 & 10, heated at 37 °C for 18 h; lane 3, periodate oxidation for 24 h at 37 °C; lane 4, pronase digestion 22 h at 37 °C ; lane 5, lipase digestion 22 h at 37 °C ; lanes 6, 7, 8, 9 precipitated antigen after TCA, acetone, chloroform-methanol or hexane-isopropanol.

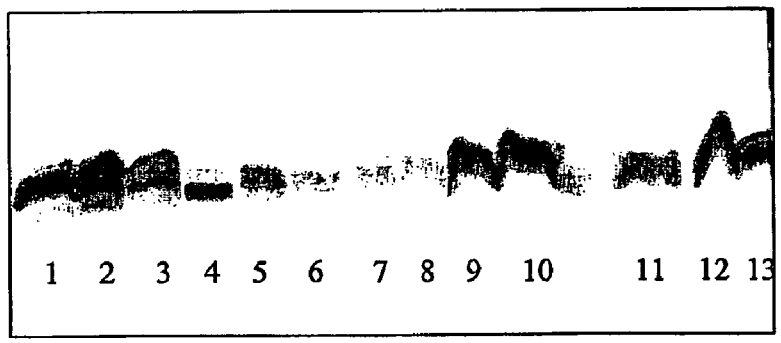

FIGURE 24. Immunoblot of Tc L3 antigen after incubation at 37 °C for 22 h with: lane 1, buffer only; 2, trypsin; 3, pepsin; 4, pronase; 5, proteinase K; 6, papain; 7, subtilisin; 8, lysing cocktail; 9, lipase; 10, lysozyme; 11, phospholipase-A2; 12, phosphoinositol-phospholipase-C; 13, phospholipase-D.

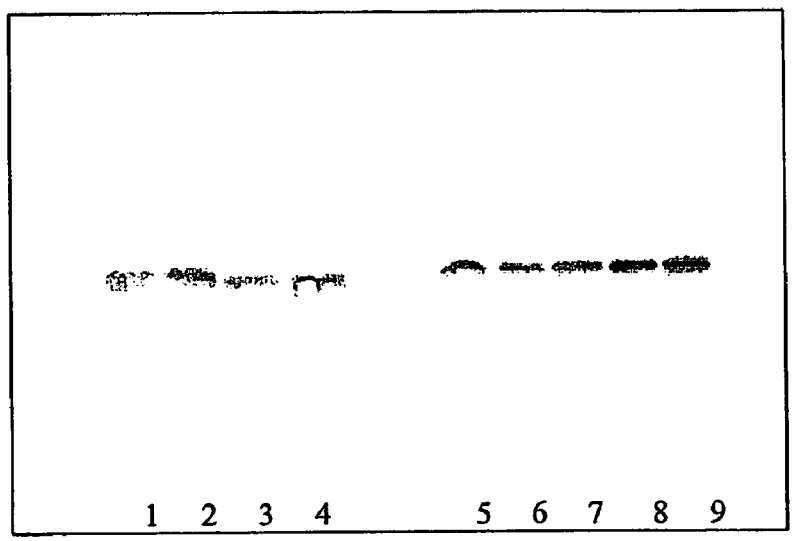
FIGURE 25. Immunoblot of Tc L3 antigen after incubation at 37 °C for 3 h with: lane 1, elastase; lane 2, collagenase; lane 3, proteinase K + SDS; lane 4, proteinase K, no SDS.
Tc L3 antigen was incubated for 18 h at 50 °C with: lane 5, buffer only; lane 6, proteinase K + SDS, DTT and EDTA; lane 7, proteinase K + SDS and EDTA; lane 8, proteinase K + SDS, DTT and Ca++; lane 9, proteinase K + SDS and Ca++.

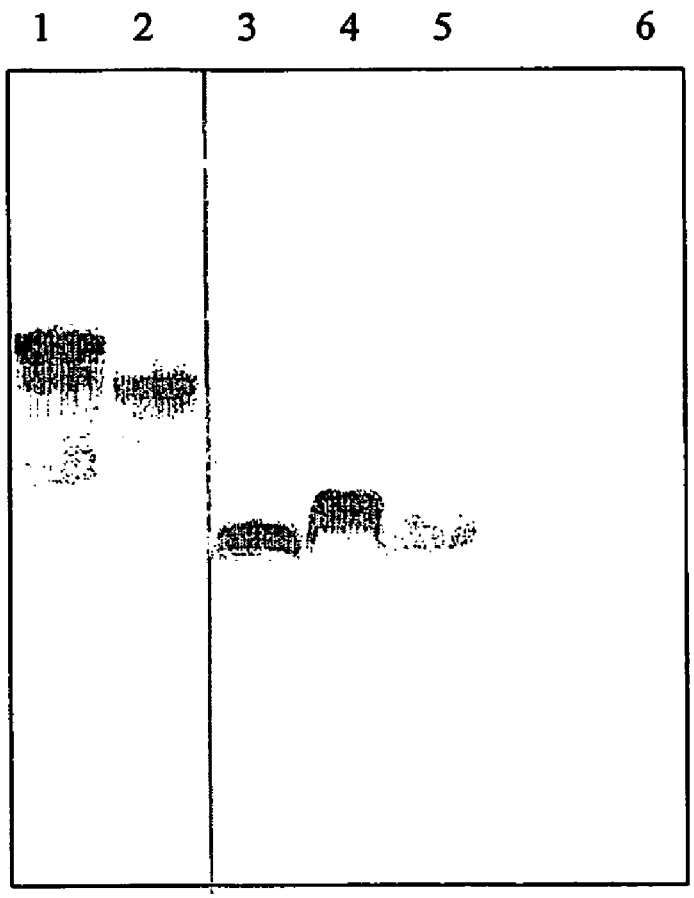

FIGURE 26. Immunoblot analysis of Tc L3 antigen and fetuin control glycoprotein after incubation with N-glycosidase F for 22 h at 37°C.

Lane 1. Untreated fetuin

Lane 2. Fetuin + N-glycosidase F

Lanes 3 & 5. Tc L3 antigen

Lane 4. Tc L3 antigen + N-glycosidase F

Fetuin was detected on the blot by reaction with digoxigenin labelled lectin SNA followed by anti-digoxigenin-HRP.

Tc antigen was detected with immune mucus and RAS/IgG-HRP.

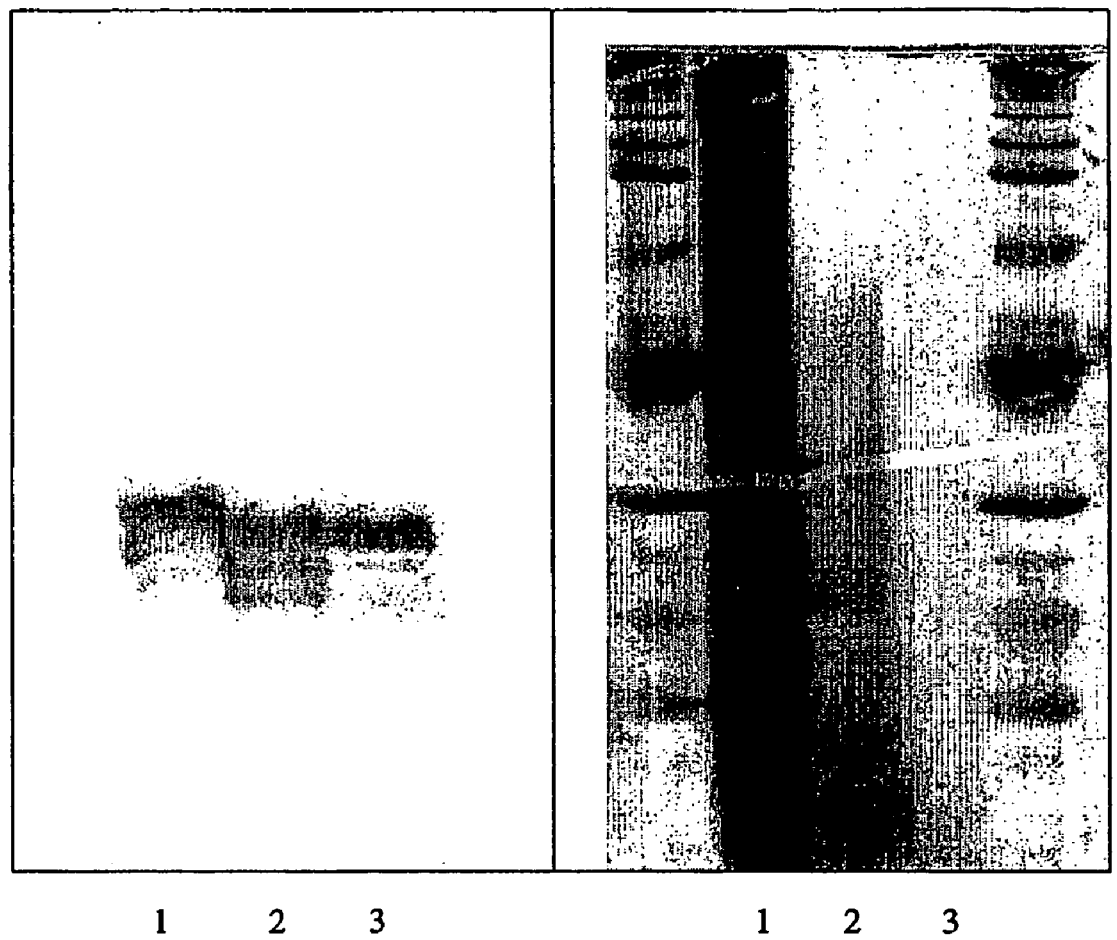
FIGURE 27. Alkaline digestion of Tc L3 antigen for 18 h at 60° C.
Lane 1, antigen control (heated only); lane 2, antigen + 1 M NaOH; lane 3, antigen + 1 M NaOH and 8 M NaBH4.
Left panel: blot probed with antibody from immune sheep mucus and RAS/IgG-HRP
Right panel: silver stain

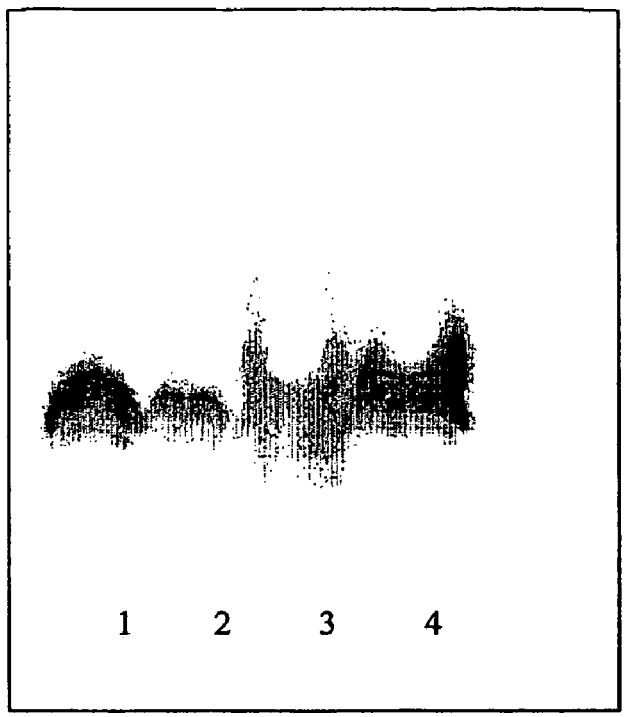

FIGURE 28. Immunoblot analysis of Tc L3 antigen after treatment with: lane 1, buffer only at 100° C for 16 h; lane 2, hydrofluorous acid for 48 h at 4° C; lane 3, hydrazine at 100° C for 16 h; lane 4, hydrazine at 20° C for 1 h.

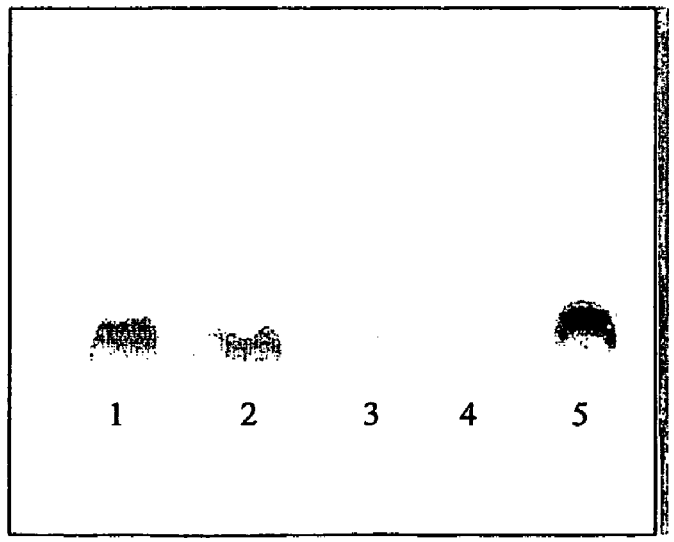

FIGURE 29. Immunoblot analysis of Tc L3 antigen after treatment with: lane 1, hydrazine at 100° C for 7 days; lane 2, hydrazine at 100° C for 14 days; lanes 3 and 4, trifluoroacetic acid for 4 h or 16 h; lane 5, untreated control.

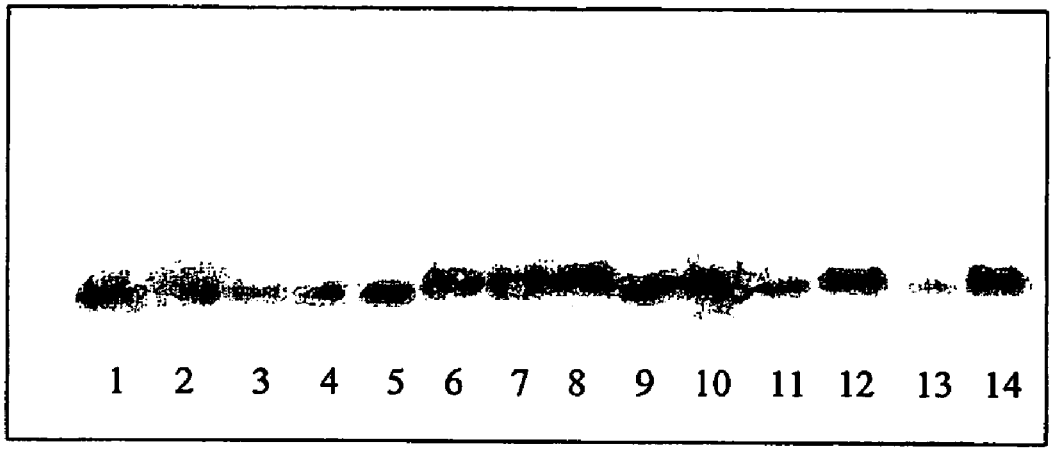

FIGURE 30. Immunoblot analysis of Tc L3 antigen after treatment by the following procedures:

lanes 1 and 2, proteinase K + SDS at 50°C for 4 h or 20 h;

lanes 3 and 6, 1 M NaOH at 37 °C for 18 h;

lane 4, heated at 90°C for 20 min then + 1 M NaOH at 37 °C for 18 h;

lanes 5 and 9, control antigen at 37 °C for 18 h;

lane 7, 0.5 M NaOH at 37 °C for 18 h;

lane 8, 0.1 M NaOH at 37 °C for 18 h;

lane 10, trypsin at 37 °C for 22 h;

lane 11, control antigen at 50°C for 22 h;

lane 12, proteinase K + SDS and DTT at 50°C for 22 h;

lane 13, heated at 90°C for 20 min then 37 °C for 18 h;

lane 14, heated at 90°C for 20 min then trypsin at 37 °C for 18 h.

Blot was probed with immune mucus followed by RAS/IgG-HRP.

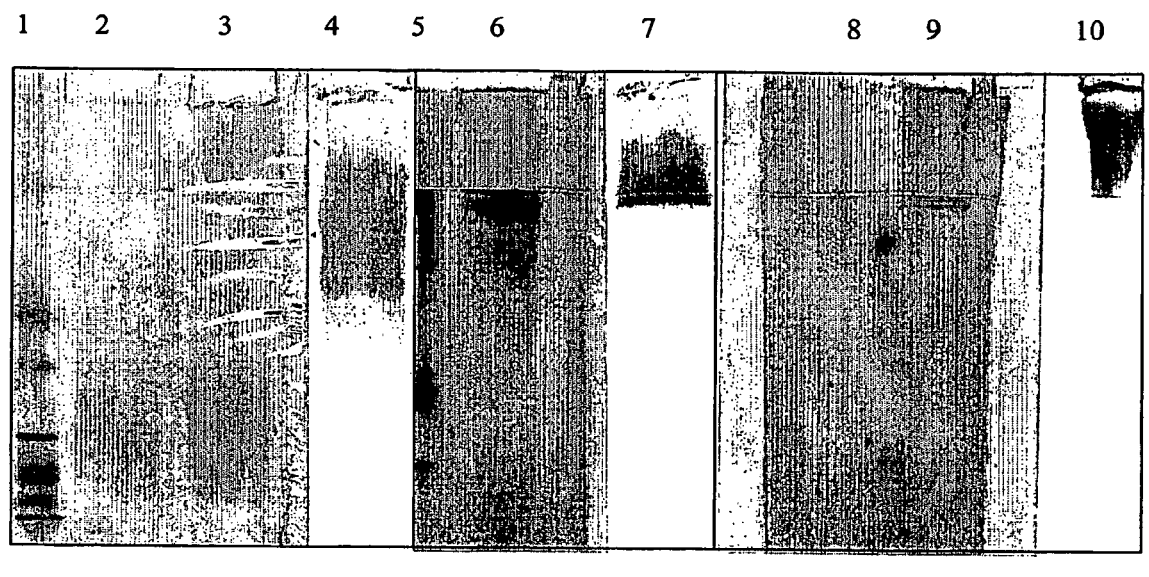

FIGURE 31. Gel electrophoresis and immunoblot analysis of Tc L3 solubilised and electrophoresed in buffer only (left panel), 6 M urea (centre) or 1 % sodium deoxycholate (right panel). Gels were stained with Coomassie blue and blots were probed with immune mucus followed by RAS/IgG-HRP.

Lanes 1, 5 & 8; protein markers

Other lanes contain Tc L3 extract in the appropriate sample buffer.

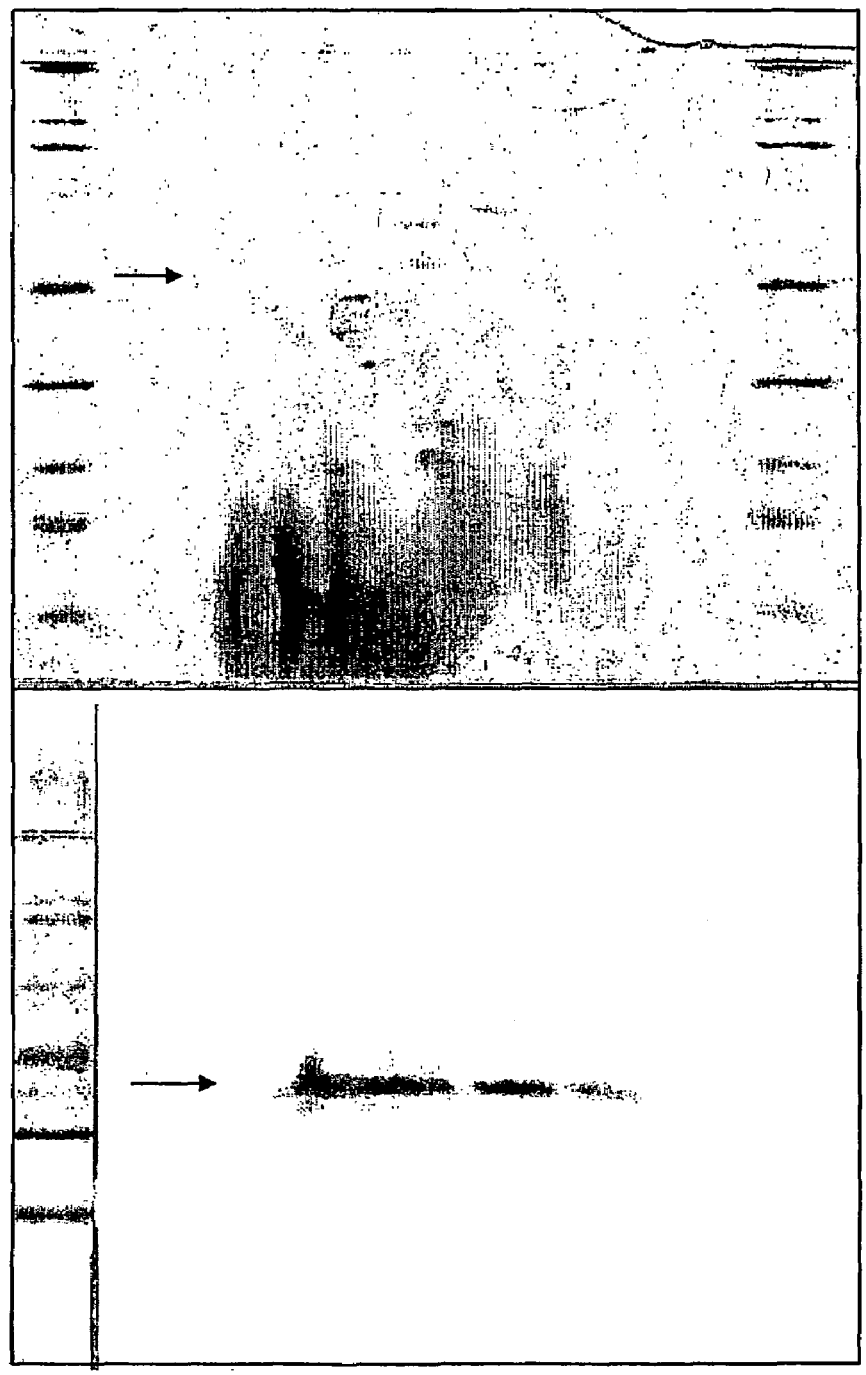
FIGURE 32. 2D electrophoresis of Tc L3 urea extract stained with Coomassie blue (top) or probed with immune mucus and RAS/IgG-HRP. Arrow shows position of 35 kDa antigen.

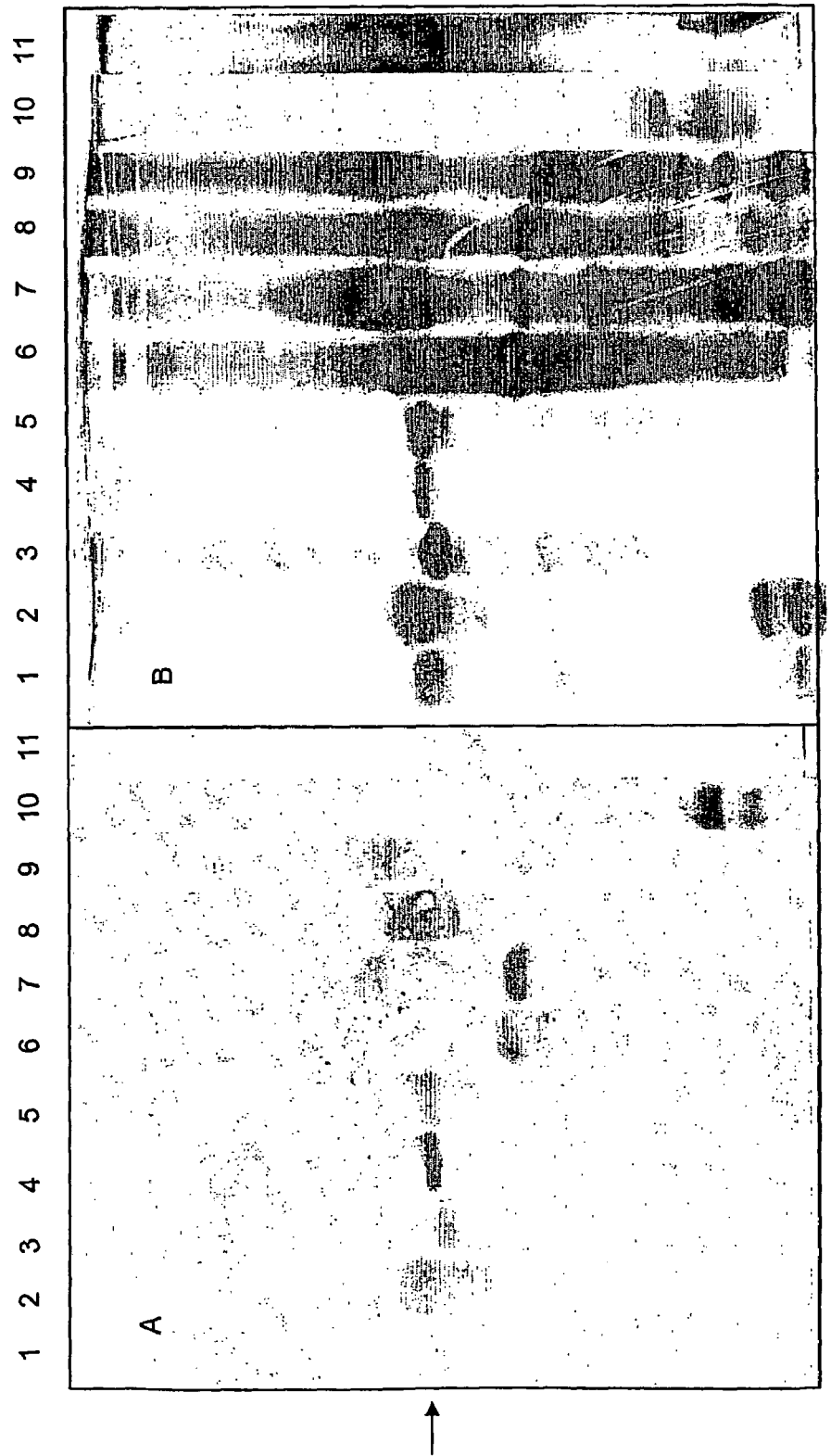

FIGURE 33. Immunoblotting analysis and carbohydrate staining of 1 M NaOH extracts from L3 of ten species of parasitic nematodes. Panel A blot reacted with intestinal mucus from *T. colubriformis* immune sheep followed by rabbit anti-sheep IgG-HRP. Panel B gel stained with carbohydrate silver stain. Lane 1, *H. contortus*. Lane 2, *O. circumcincta*. Lane 3, *T. axei*. Lane 4, *T. colubriformis*. Lane 5, *T. vitrinus*. Lane 6, *N. spathiger*. Lane 7, *C. curticei*. Lane 8, *O. ostertagi*. Lane 9, *C. oncophera*. Lane 10, *N. brasiliensis* Lane 11, *D. eckerti*.Arrow marks position of 35 kDa antigen.

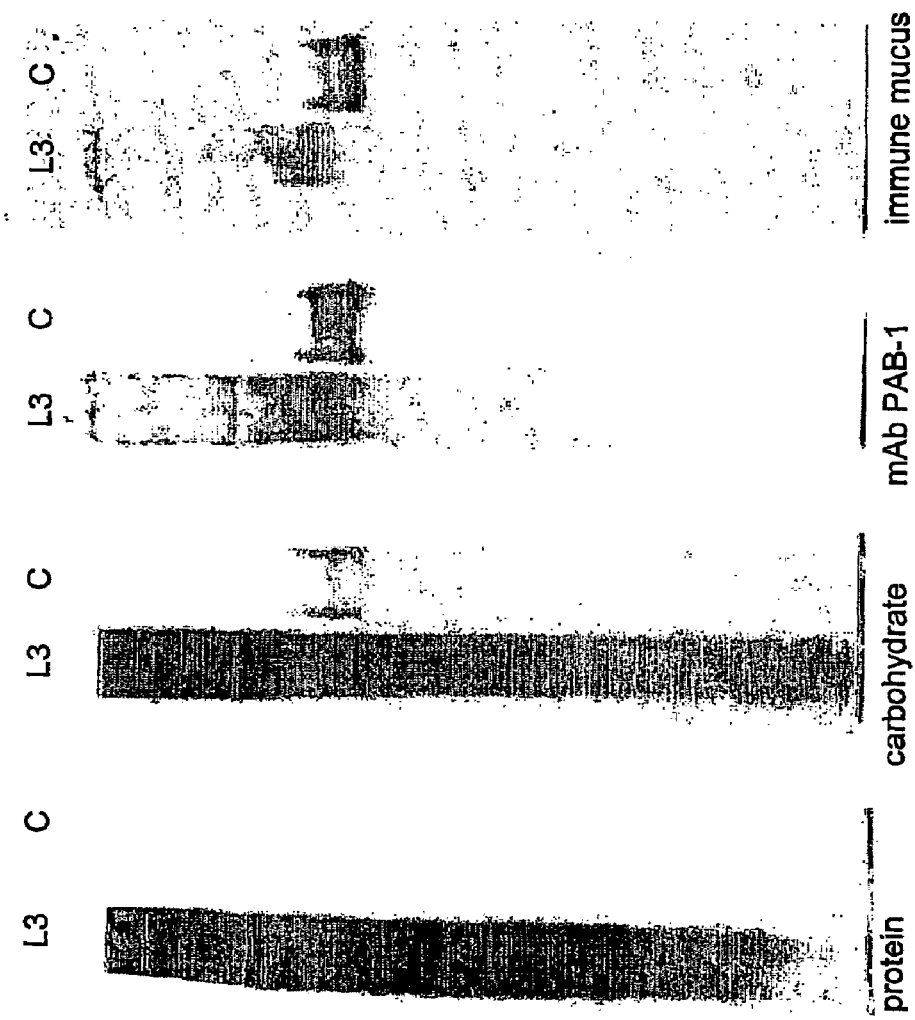

FIGURE 34. Gel electrophoresis (8 % PAGE) and immunoblot analysis of *T. colubriformis* L3 extract (L3) and purified carbohydrate larval antigen (C) run under non-denaturing conditions (no detergent or reducing agent). Gels were stained for protein or carbohydrate. Blots were reacted with mAb PAB-1 followed by rabbit anti-mouse Ig-HRP conjugate, or with immune sheep mucus followed by rabbit anti-sheep Ig-HRP conjugate.

MONOCLONAL ANTIBODY AND NEMATODE LARVAL ANTIGENS

RELATED APPLICATIONS

This is the United States National Phase under 35 U.S.C. 371 of International Application PCT/NZ03/00010, filed Jan. 30, 2003.

TECHNICAL FIELD

The present invention relates to a monoclonal antibody and nematode larval antigens. In particular the present invention relates to a monoclonal antibody specific for surface antigens on third stage larvae (L3) of parasitic nematodes.

BACKGROUND ART

The infestations by nematode parasites of animals such as sheep and cattle are of economic importance to those in the agriculture industry. Traditionally, nematode infection has been treated by the administration of anthelmintics.

However, a major drawback with conventional anthelmintics is that nematode resistance to a broad spectrum of anthelmintics is now becoming increasingly more widespread and is therefore of serious concern (Waller, 1997; Sangster et al, 1999; Van Wyk et al, 1999)

A number of mechanisms have been proposed to explain expulsion of nematodes from the intestine of immune sheep (Rothwell 1989). There is evidence for the involvement of elements of an immediate hypersensitivity response, where antigenic stimulation of IgE-sensitised mucosal mast cells leads to an accumulation of substances in mucus which may affect nematode survival (Miller 1996; Emery et al 1997). Anti-nematode properties of mucus include the presence of chemical mediators (Douch et al 1983; Jones et al 1990) and antibody (Lee & Ogilvie 1981; Miller 1987; Carlisle et al 1991). Recently, the present inventors showed that intestinal mucus obtained from sheep immunised by multiple truncated infections could alter the normal pattern of larval establishment after infusion of a mixture of larvae and mucus into the duodenum of naive recipient sheep (Harrison et al 1999). Mucus collected from the small intestine of sheep immune to the parasitic nematode *Trichostrongylus colubriformis* was found to have anti-larval activity, causing larvae to clump in vitro and resulting in significant reduction of numbers of larvae establishing in naive sheep after infusion of larvae and mucus via a duodenal cannula.

Immunoblotting showed that immune mucus contained IgG and IgA antibodies that recognised predominantly an antigen with an estimated molecular weight of 35 kDa. Antibodies eluted from the surface of larvae incubated in immune mucus also reacted with the 35 kDa antigen on blots of larval homogenate. Immunofluorescence and immunogold electron microscopy showed that the 35 kDa antigen was present on the epicuticle of L3 and was shed during the moult to L4. The antigen was not present in eggs, L1, L2, L4 or adult worms and was only seen in extracts of L3 before infection and up to 5 days after infection. The results suggest that the binding of antibody to the larval surface prevented larvae from establishing at their preferred site, causing them to be eliminated from the intestine. Immunisation of sheep with partially purified 35 kDa antigen resulted in a significant reduction of egg count following challenge with *T. colubriformis*, indicating the potential usefulness of this antigen in a vaccine.

A monoclonal antibody designated PAB-1 was prepared against the larval surface antigen. MAb PAB-1 and sheep mucus antibody both recognised the 35 kDa *T. colubriformis* larval antigen and also cross reacted with an antigen of similar molecular weight on blots of L3 extracts of the parasitic nematodes *Haemonchus contortus* and *Ostertagia circumcincta*; and with a 22 kDa antigen on blots of L3 antigens extracted from *Cooperia curticei* and *Nematodirus spathiger*. This indicated that a common surface antigen with immunising potential was present on other nematode species and could be identified by mAb PAB-1. The 35 kDa larval antigen and related molecules are likely to be novel targets for host immunity and can thus be utilised in a vaccine or other immunotherapy against nematode infections.

Monoclonal antibody PAB-1 can be used to immunopurify the surface antigen by standard affinity chromatography techniques. Monoclonal antibody PAB-1 coupled to a solid phase support such as agarose or sepharose binds the surface antigen from a crude extract of L3. The surface antigen can be eluted from the antibody matrix using a low pH buffer and shown to be substantially pure by SDS PAGE. The surface antigen purified in this manner is detected by immunoblotting against sheep antibody from immune mucus and can be stained by methods used for detecting carbohydrates.

The 35 kDa larval antigen and related molecules are known to have a predominantly carbohydrate structure. This is because the antigen is resistant to digestion by proteinase K: does not stain in gels treated with sensitive protein stains; does stain with carbohydrate stains and can be labelled with carbohydrate labelling reagents such as biotin-hydrazide.

Accordingly, mAb PAB-1 may be useful in identifying and isolating the surface antigen for development into a vaccine or other immunotherapy against nematode infections.

Serum and intestinal mucus from sheep infected with *T. colubriformis* contains antibody that recognises the 35 kDa larval antigen and related molecules. Accordingly, as the presence of antibody to the larval antigen indicates exposure to the parasite, monoclonal antibody PAB-1 may be useful as a diagnostic tool for the identification of infected animals.

All references, including any patents or patent applications, cited in this specification are hereby incorporated by reference. No admission is made that any reference constitutes prior art. The discussion of the references states what their authors assert, and the applicants reserve the right to challenge the accuracy and pertinency of the cited documents. It will be clearly understood that, although a number of prior art publications are referred to herein, this reference does not constitute an admission that any of these documents forms part of the common general knowledge in the art, in New Zealand or in any other country.

SUMMARY OF INVENTION

According to a first aspect of the present invention there is provided an isolated monoclonal antibody mAb PAB-1, deposited at ATCC on 24 Jan. 2002 and accorded accession PTA-4005, which binds to a surface antigen on nematode L3.

According to a second aspect of the present invention there is provided an isolated monoclonal antibody as described above wherein the antibody binds to an antigen sourced from *T. colubriformis* L3, wherein in said antigen runs at substantially 35 kDa on SDS PAGE gel under reducing conditions.

According to a third aspect of the present invention there is provided an isolated monoclonal antibody as described above wherein the antibody binds to surface antigens on L3 selected from the group consisting of:
  a) a surface antigen on *C. curticei* which runs at substantially 46 kDa and at substantially 22 kDa on SDS PAGE gel under reducing conditions;
  b) a surface antigen on *N. spathiger* which runs at substantially 22 kDa on SDS PAGE gel under reducing conditions;
  c) a surface antigen on *H. contortus* which runs at substantially 35 kDa on SDS PAGE gel under reducing conditions; and
  d) a surface antigen on *O. circumcincta* which runs at substantially 35-39 kDa on SDS PAGE gel under reducing conditions;
  e) a surface antigen on *T. axei* or *T. vitrinus* which runs at substantially 35 kDa on SDS PAGE gel under reducing conditions;
  f) a surface antigen on *O. ostertagi* which runs at substantially 30-45 kDa on SDS PAGE gel under reducing conditions;
  g) a surface antigen on *C. oncophera* which runs at substantially 20 kDa and at substantially 45 kDa on SDS PAGE gel under reducing conditions;
  h) a surface antigen on *N. brasiliensis* which runs at substantially 9 kDA and at substantially 12 kDa on SDS PAGE gel under reducing conditions;
  i) a surface antigen on *D. eckerti* which runs at substantially 30 kDa on SDS PAGE gel under reducing conditions.

According to a fourth aspect of the present invention there is provided an isolated monoclonal antibody as described above wherein the antibody when coupled to a solid support can be utilised to purify the surface antigen by immunoaffinity chromatography.

According to a fifth aspect of the present invention there is provided an isolated carbohydrate surface antigen from a nematode L3, wherein the antigen binds to monoclonal antibody mAb PAB 1, deposited at ATCC on 24 Jan. 2002 and accorded accession PTA-4005.

Most preferably said antigen also resists boiling in 1 M NaOH.

According to a sixth aspect of the present invention there is provided an isolated antigen substantially as described above wherein the antigen runs at substantially between 20-35 kDa or at substantially 9 kDa and 12 kDa on SDS PAGE gel under reducing conditions.

According to a seventh aspect of the present invention there is provided an isolated antigen substantially as described above wherein the antigen is sourced from *T. colubriformis* L3.

According to an eighth aspect of the present invention there is provided an isolated antigen substantially as described above wherein the antigen is sourced from nematode L3 isolated from the group consisting of *C. curticei, N. spathiger, H. contortus, O. circumcincta, T. axei, T. vitrinus, O. ostertagi, C. oncophera, N. brasiliensis* and *D. eckerti*.

According to a ninth aspect of the present invention there is provided a composition that comprises an antigen substantially as described above together with a pharmaceutically or veterinarily acceptable carrier or diluent.

According to a tenth aspect of the present invention there is provided the use of an antigen substantially as described above in the manufacture of a composition for preventing, treating, or reducing the susceptibility to, nematode infection.

According to an eleventh aspect of the present invention there is provided the use of a composition substantially as described above for preventing, treating, or reducing the susceptibility to, nematode infection in susceptible sheep from nematodes selected from the group consisting of *T. colubriformis, C. curticei, N. spathiger, H. contortus, O. circumcincta T. axei, T. vitrinus, O. ostertagi, C. oncophera, N. brasiliensis* and *D. eckerti*.

According to a twelfth aspect of the present invention there is provided a composition substantially as described above for preventing, treating, or reducing the susceptibility to, nematode infestation in susceptible animals other than sheep wherein these other species of nematodes also possess a larval surface antigen identified by reaction with monoclonal antibody PAB-1 as described above.

Preferably, these other animals, may be any animals susceptible to nematode infection as a foresaid, and may include mice, rats, guinea pigs, rabbits, goats, sheep, horses, pigs, dogs, cats, chickens, cattle, deer or the like.

According to a thirteenth aspect of the present invention there is provided a composition substantially as described above wherein the composition also includes at least one adjuvant or cytokine.

According to a fourteenth aspect of the present invention there is provided a method of diagnosing nematode infection in susceptible animals comprising the steps of:
  a) obtaining a blood sample from an animal; and
  b) analysing the sample for the presence of an antibody against the antigens described in the third aspect of the invention above via a suitable assay.

Preferably, the assay may be an ELISA or western blotting assay although this should not be seen as limiting as other types of assay are envisioned.

According to a fifteenth aspect of the present invention there is provided an isolated antibody substantially as described above wherein the antibody has been sourced from the gastrointestinal mucus of animals which has been immunised by truncated infections with nematodes selected from the group consisting of *T. colubriformis, C. curticei, N. spathiger, H. contortus, O. circumcincta T. axei, T. vitrinus, O. ostertagi, C. oncophera, N. brasiliensis* and *D. eckerti*.

According to a sixteenth aspect of the present invention there is provided a method of preventing or treating animal nematode infections, by administering the composition of the present invention.

According to a seventeenth aspect of the present invention there is provided the use of an antigen of the present invention to elicit an antibody response in the gut mucus of sheep or other susceptible animals to treat, prevent or reduce susceptibility to, nematode infections in sheep.

According to an eighteenth aspect of the present invention there is provided a use for monoclonal antibody substantially as described above to detect nematode infection in sheep.

The term "isolated" means that the monoclonal antibody or carbohydrate of the present invention is removed from its original environment and is separated from some or all of the co-existing materials in the natural system from which the antibody or carbohydrate has been obtained.

The term "L3" refers to a particular larval stage of development in a nematode life cycle.

The term 35 kDa antigen generally refers, unless context dictates otherwise, to the *T. Colubriformis* antigen which runs at substantially this molecular weight. The term "susceptible animal" refers to sheep prone to nematode infection by the following species of nematode *T. colubriformis, C. curticei, N. spathiger, H. contortus, O. circumcincta, T. axei,*

*T. vitrinus, O. ostertagi C. oncophera, N. brasiliensis* and *D. eckerti* or to other animals prone to nematode infection where those nematodes possess an antigen detected by monoclonal antibody PAB-1 as described.

DISCLOSURE OF INVENTION

The monoclonal antibody of the present invention is a monoclonal antibody which recognises carbohydrate surface antigens on L3 of parasitic nematodes. The monoclonal antibody has been found by the inventors to have the same specificity as the anti-larval antibody present in intestinal mucus from sheep immunised against *T. colubriformis*. A hybridoma producing monoclonal antibody mAb PAB-1 was deposited at ATCC on 24 Jan. 2002 and accorded accession PTA-4005.

The following outlines in general non-limiting terms the procedures for identifying and producing the antibody of the present invention.

Sheep prone to nematode infection were raised nematode free from birth till four months old when a set number were immunised by a series of truncated infections with *T. colubriformis* L3. The remainder of the immunised sheep continued to be raised under nematode free conditions. Preferably the sheep to be used were subjected to 3 truncated infections over a period of time, each infection being terminated after a set time frame. Preferably, the set time frame may be 14 days with re-infection occurring approximately 7 days after termination, although it should be appreciated that these time frames should not be seen as limiting.

After termination of the last infection the sheep were slaughtered and mucus was obtained from the small intestine, substantially in accordance with the method of Harrison et al, 1999, although this method should not be seen as limiting, as other methods may also be employed. Mucus from naïve sheep was also taken as outlined above.

Once obtained, immune and naïve mucus samples were then analysed for differences in protein profiles, for example by SDS PAGE gel and staining with Coomassie blue or silver.

The mucus antibody can then be characterised. Preferably this may be achieved by immunoblotting L3 homogenate antigen and probing with immune and naïve mucus samples. Antibody binding may be detected by reaction with commercially available antisera raised against sheep immunoglobulins and conjugated with an enzyme. Preferably, the antibody binding may be detected by RAS/IgG-HRP.

The L3 homogenate may be prepared by disruption of exsheathed L3 of any of the parasitic nematode species listed herein, using mechanical or chemical means, in the presence or absence of suitable detergents or denaturants, followed by clarification of the extract by centrifugation and/or filtration.

Most preferably the L3 homogenate may be prepared by disruption of exsheathed L3 of *T. colubriformis* frozen in liquid $N_2$, using a mortar and pestle to grind the frozen L3 until disrupted. Larval components are then extracted into a neutral buffer e.g. 50 mM Tris-HCl pH 7.5 containing 1-2% of a solubilising agent such as CHAPS, sodium deoxycholate, urea or SDS. The extract is clarified by centrifugation at 100 000×g for 1 h or by filtration through a series of membranes with decreasing pore size e.g. 5.0 μm down to 0.2 μm.

The method for producing the monoclonal antibody mAb PAB-1 may be any suitable method such as that of Kohler and Milstein (1975).

For example, the 35 kDa antigen may be excised from polyacrylamide gel slices, macerated and mixed with equal volumes of an incomplete oil adjuvant and then administered to the abdominal cavity, subcutis, footpads or the like of an animal to be immunized such as mouse, rat, guinea pig, rabbit, goat, sheep, horse, pig, dog, cat, chicken, cattle, deer or the like. Among these animals preferably a mouse is used.

Antibody producing cells such as spleen cells, lymphocytes or peripheral blood cells may be collected from the immunized animal, and fused with myeloma cells, (a tumor cell strain) to form a hybridoma. Spleen cells are preferable as antibody producing cells.

The myeloma cells used for the cell fusion are preferably those cell lines allogenic to the immunized animal. However, cell lines of various animals can also be used.

Preferably, NS-1 cells may be used as the myeloma cells. However, this should not be seen as limiting the scope of the present invention.

Though the monoclonal antibody of the present invention is typically an antibody produced by a hybridoma, antibody fragments obtained by treating such an antibody with a protease not degrading the antigen-binding site (Fab) such as plasmin, pepsin and papain, i.e., Fab, $F(ab')_2$, Facb and the like, or antibody fragments produced by molecular cloning techniques, are encompassed by the monoclonal antibody of the present invention, so long as they have the properties of the monoclonal antibody of the present invention.

The carbohydrate surface antigen of the present invention is found on the surface of L3 of *T. colubriformis, C. curticei, N. spathiger, H. contortus, O. circumcincta, T. axei, T vitrinus, O. ostertagi C. oncophera, N. brasiliensis* and *D. eckerti*.

The following outlines in general non-limiting terms the procedures for identifying and isolating the carbohydrate antigen of the present invention.

The carbohydrate surface antigen of the present invention can be isolated from extracts of L3 of the nematodes listed herein. Preferably, the carbohydrate antigen may be isolated from extracts of *T. colubriformis* L3 prepared as described above. Monoclonal antibody PAB-1 may be first coupled to a solid phase support medium, preferably Protein A-agarose or Protein G-agarose and covalently linked to prevent antibody leakage from the gel.

The gel may then be packed into a chromatography column and L3 extract applied. After washing with a neutral buffer, preferably PBS containing 0.05% Tween 20 to prevent non-specific binding, the bound carbohydrate antigen can be eluted from the column by applying an elution buffer of high or low pH or high salt concentration. Preferably, glycine-HCl buffer pH 2.5-2.8 may be used to elute the antigen. After elution, the pH of the carbohydrate antigen can be raised to neutrality by addition of 1 M tris. The carbohydrate antigen is then identified by further analysis using electrophoresis and blotting against antibody from immune sheep mucus. The nature of the carbohydrate antigen may be determined by staining with a carbohydrate detecting silver stain and by labelling on blots with the carbohydrate-binding reagent biotin-hydrazide.

It will be appreciated by those skilled in the art that other carbohydrate detecting methods may also be used. Such methods may include but should not be limited to lectin binding, HPLC, TLC, fluorophore assisted carbohydrate electrophoresis, MS and NMR.

Methods and pharmaceutical carriers for preparation of pharmaceutical compositions are well known in the art, as set out in textbooks such as Remington's Pharmaceutical Sciences, 19th Edition, Mack Publishing Company, Easton, Pa., USA.

The compounds, vaccines and compositions of the invention may be administered by any suitable route, and the person skilled in the art will readily be able to determine the most suitable route and dose for the condition to be treated. Dosage will be at the discretion of the attendant physician or veterinarian, and will depend on the nature and state of the condition to be treated, the age and general state of health of the subject to be treated, the route of administration, and any previous treatment which may have been administered.

The carrier or diluent, and other excipients, will depend on the route of administration, and again the person skilled in the art will readily be able to determine the most suitable formulation for each particular case.

For the purposes of this specification it will be clearly understood that the word "comprising" means "including but not limited to", and that the word "comprises" has a corresponding meaning.

BRIEF DESCRIPTION OF DRAWINGS

Further aspects of the present invention will become apparent from the following description which is given by way of example only and with reference to the accompanying drawings in which:

FIG. 1 Shows the number of larvae in naïve sheep after incubating larvae with various amounts of mucus from naïve sheep or mucus from immune sheep;

FIG. 2 Shows the numbers of larvae in naïve sheep after incubating larvae with mucus from naïve or immune sheep for various times;

FIG. 3 Shows the number of larvae in proximal and distal sections of naïve sheep intestine after infusing naïve recipient sheep with mixtures of L3 in naive or immune mucus;

FIG. 4 Shows the anti-larval activity of immune mucus at various times after immunisation;

FIG. 5 Shows the results of an SDS PAGE analysis of immune and naïve mucus;

FIG. 6 Shows the results of lectin blotting of immune and naïve mucus.

A: UEA-1 (α-L-frucose). B: JAC (α-gal-Me-pyranoside)
C: WGA (N-acetylglucosamine) D: LL (mannose, glucose)

FIG. 7 Shows the results of lectin blotting of immune and naïve mucus.

A: PNA (β-galactose-N— acetylgalactosamine)
B: EcorA (β-galactose-N-acetylglucosamine)
C: SBA (N-acetylgalactosamine)
D: ECA (β-galactose-N-acetylgalactosamine)

FIG. 8 Shows the results of lectin blotting of immune and naïve mucus

A: SNA (sialic acid)
B: immunoblot probed with RAS/IgG-HRP

FIG. 9 Shows the results of an immunoblot of T. colubriformis L3 antigen probed with intestinal mucus from immune sheep (lanes 1, 5, 10, 11, 12 and 19) or naïve sheep (lanes 13-18), 100 000×g supernatant of immune mucus (lane 3), immune mucus supernatant purified from Protein G-agarose (lanes 4 and 7), antibody eluted from exsheathed T. colubriformis L3 (lanes 6 and 20), antibody from ammonium sulphate precipitated gut lumen fluids from immune sheep (lanes 8 and 9). Lane 2 shows T. colubriformis L3 proteins stained with colloidal gold. IgG antibody was detected with RAS/IgG-HRP (lanes 1-18) and IgA was detected with MAS/IgA followed by RAM/IgG-HRP (lanes 19 and 20).

FIG. 10 Shows the results of T. colubriformis L3 antigen probed with naïve or immune mucus. Antigen strips were reacted with naïve mucus or immune mucus followed by either RAS/IgG; mAB to sheep $IgG_1$; mAB to sheep $IgG_2$; mAB to sheep IgA; mAB to sheep IgM FIG. 11 Shows the results of an immunoblot of T. colubriformis L3 antigen, C. curticei L3 antigen and N. spathiger L3 antigen.

FIG. 12 Shows the results of an immunoblot analysis of extracts from L3 of H. contortus, O. circumcincta, N. spathiger, C. curticei and T. colubriformis.

FIG. 13 Shows the correlation of protection against infection with intestinal mucus IgG and IgA antibody titre against T. colubriformis L3 antigen.

FIG. 14 Shows the decline of IgG and IgA antibody titres in intestinal mucus over time.

FIG. 15 Shows exsheathed T. colubriformis L3 reacted with immune or naïve mucus (top panels) and shows T. colubriformis larvae collected 5 days after infection and reacted with immune mucus (lower panels).

FIG. 16 Shows electronmicrographs of exsheathed T. colubriformis L3 after reaction with naïve (A) or immune mucus (B). Panels C-F show T. colubriformis larvae collected at 2, 3, 4 or 5 days after infection and reacted with immune mucus.

FIG. 17 Shows the results of SDS PAGE and immunoblotting analysis of T. colubriformis eggs, larvae and adults. Panels A, C and D reacted with immune mucus. Panel B silver stained proteins.

FIG. 18 Shows the results of SDS PAGE and immunoblotting analysis of T. colubriformis L3 before infection and at various times after infection.

FIG. 19 Shows the results of an immunoblot analysis of T. colubriformis L3 extracts and proteinase K digested L3 extracts reacted with immune mucus or monoclonal antibody PAB-1.

FIG. 20 Shows an immunoblot analysis of L3 antigen extracts and proteinase K digested L3 extracts from five nematode species reacted with monoclonal antibody PAB-1.

FIG. 21 Shows surface fluoresence of exsheathed T. colubriformis L3 reacted with control monoclonal antibody (left and centre panels) or with monoclonal antibody PAB-1 (right panel).

FIG. 22 Shows analysis of Tc larval surface antigen purified by immuno-affinity chromatography using monoclonal antibody PAB-1.

FIG. 23 Shows the results of an immunoblot analysis of T. colubriformis L3 extracts after heating, oxidation, digestion or precipitation by organic solvents.

FIG. 24 Shows the results of an immunoblot analysis of T. colubriformis L3 extracts after digestion by proteases or lipases.

FIG. 25 Shows the results of an immunoblot analysis of T. colubriformis L3 extracts after digestion by proteases.

FIG. 26 Shows the results of an immunoblot analysis of T. colubriformis L3 extracts after digestion by glycosidase.

FIG. 27 Shows the results of an immunoblot analysis of T. colubriformis L3 extracts after alkaline degradation.

FIG. 28 Shows the results of an immunoblot analysis of T. colubriformis L3 extracts after heating and alkaline or acid degradation.

FIG. 29 Shows the results of an immunoblot analysis of T. colubriformis L3 extracts after heating and alkaline or acid degradation.

FIG. 30 Shows the results of an immunoblot analysis of *T. colubriformis* L3 extracts after heating, alkaline degradation or protease digestion.

FIG. 31 Shows the results of an immunoblot analysis and protein stain of *T. colubriformis* L3 extracts after electrophoresis under native conditions or in the prsence of urea or sodium deoxycholate.

FIG. 32 Shows the results of an immunoblot analysis and protein stain of *T. colubriformis* L3 extract after 2-dimensional electrophoresis.

FIG. 33 Shows the presence of carbohydrate staining molecules in L3 extracts of 6 additional nematodes.

FIG. 34 Shows a Gel electrophoresis (8% PAGE) and immunoblot analysis of *T. colubriformis* L3 extract (L3) and purified carbohydrate larval antigen (C) run under non-denaturing conditions (no detergent or reducing agent).

BEST MODES—FOR CARRYING OUT THE INVENTION

1. Materials and Methods 1.1 Sheep Immunisation by Truncated Infections

All sheep experiments were conducted with the approval of Wallaceville Animal Ethics Committee. Romney sheep were raised nematode-free from birth, housed in pens and fed commercial sheep pellets, hay and water ad lib. Sheep were at least 4 months old at the start of the immunising infections. Sheep were immunised by truncated infections with 40 000 *T. colubriformis* L3 on at least three occasions. Each infection was terminated after 14 days by oral drenching with oxfendazole (Systamex, Schering Plough Ltd., 4.5 mg kg$^{-1}$) and sheep were re-infected 7 days after drenching. In some experiments, sheep were given a fourth infection (booster dose), which was not terminated by drenching, as these sheep were slaughtered 2-3 days after boosting.

1.2. Sample Collection

Sheep were slaughtered by captive bolt gun and exsanguination. The small intestine was tied off into 5 m sections and each section was washed through with 4×150 ml saline to collect larvae. For biochemical analysis and in vivo challenges, mucus was collected from the first 6 m of small intestine and processed as described (Harrison et al 1999) with the following modifications. After gentle rinsing with 100 ml saline to remove gut contents, the intestine was held at 4° C. for 2 h and mucus was then squeezed out by firm pressure between thumb and finger, followed by 2×5 ml washes with saline. Mucus and washings were pooled and processed as described (Harrison et al 1999) and stored at −20° C.

Biopsy samples of mucus were collected from groups of 4 truncated infection sheep at 3 days, 16 days and 35 days after the last immunisation. At surgery, the duodenum was located and a 5 cm section was isolated by gentle clamping with forceps. 3 ml saline was injected using a blunt ended 18-gauge needle. The liquid was teased back and forth 10 times to mix mucus with the saline and a 2-3 ml sample was then withdrawn. The incision was closed and the sheep allowed to recover.

1.3 Effect of Various Treatments on Mucus Activity In Vitro

Ability of mucus to bind larvae was assessed by a larval clumping test where 2000 exsheathed L3 were incubated with 0.4 ml mucus in an Eppendorf tube at 37° C. on a rocking platform. After 4 h, samples were examined and the degree of larval clumping was estimated, compared to controls of L3 incubated with naive mucus or saline.

Immune mucus was subjected to various treatments and then analysed for larval clumping activity. Aliquots of 1 ml immune mucus IP5 were dialysed for 24 h against saline at 4° C.; centrifuged at 10 000×g, 50 000×g or 100 000×g; heated at 60° C. or 100° C. for 5 min; reduced and alkylated by treatment with 10 mM DTT for 1 h then reaction with 20 mM iodoacetamide for 30 min on ice followed by dialysis against TBS pH 7.4 overnight to remove excess salts. For pepsin treatment, mucus was adjusted to pH 4.5 with 1 M HCl and 3 mg pepsin in 0.1 M acetate buffer pH 4.5 was added to 3 ml mucus and incubated for 20 h at 37° C. on a rocking platform. The reaction was stopped by adding tris to 2 M. Protease treatment was conducted by adding 1 mg pronase in 0.1 M tris pH 7.5 to each ml of mucus and incubating for 20 h at 37° C. on a rocking platform. The reaction was stopped by adding protease inhibitors. Mucus was treated with 1 mg lipase in PBS pH 7.2 per ml mucus, incubated at 37° C. for 20 h, then stored frozen. Mucus was oxidised by adjusting the pH to 4.5 with acetic acid, adding periodate to 20 mM in 50 mM sodium acetate buffer pH 4.5 and incubating in the dark at RT for 2 h with stirring. Sodium borohydride was then added to 50 mM and incubated for 1 h with stirring. Mucus was ultra filtered by diluting 5 ml immune mucus IP5 into 250 ml PBS pH 7.2 and concentrating back to 5 ml on a Filtron 100 000 mw membrane. The filtrate was then concentrated to 5 ml on a 10 000 mw membrane and this filtrate was reduced to 5 ml on a 3 000 mw membrane. The low mw filtrate was lyophilised, redissolved in 5 ml d.H$_2$O and dialysed in 1 000 mw tubing against d.H$_2$O.

After treatment as described above, mucus samples were stored frozen until assayed.

1.4 In Vivo Mucus Assay 40 000 exsheathed L3 were incubated with 2.5-10 ml volumes of immune or naive mucus for 4-24 h before infusion into the duodenum of parasite-naive sheep via a surgically implanted catheter (Harrison et al 1999). One week later, sheep were slaughtered and the numbers of larvae establishing in each 5 m section of intestine were estimated.

40 000 exsheathed L3 were incubated at 37° C. for 4 h with 10 ml volumes of immune or naive mucus, or with 2×10 ml volumes of mucus supernatant after centrifugation at 100 000×g. After incubation, one aliquot of naïve and immune supernatant was centrifuged at 200×g for 3 min to pellet the larvae. The supernatant was removed by aspiration and the L3 were washed with 10 ml saline, centrifuged as above, the supernatant removed and the 13 resuspended in 10 ml saline. Each 10 ml aliquot was then infused via a duodenal cannula, into the intestine of a naïve sheep. One week later, the sheep were slaughtered and larval counts obtained.

1.5 Biochemical Analysis of Mucus

A panel of immune and naive mucus samples was analysed for differences in protein profiles by SDS PAGE and staining with Coomassie blue or silver. Differences in glycosylation were examined by lectin blotting using biotin labelled lectins, detected by streptavidin-peroxidase. Presence of IgG in mucus was demonstrated by blotting against RAS/IgG-HRP.

1.6 Characterisation of Mucus Antibody

Immunoblots of L3 homogenate antigen were probed with immune and naive mucus samples. Antibody binding was detected with RAS/IgG-HRP, or with mAb's to sheep $IgG_1$, $IgG_2$, IgM and IgA, followed by GAM/Ig-HRP.

Exsheathed L3 were incubated for 4 h at 37° C. with mucus supernatant, 45% ammonium sulphate precipitated antibody from mucus or Protein G purified antibody from mucus. After incubation, larvae were washed 3 times with TBS-Tw and any bound antibody was eluted by incubation for 5 mins in 0.1 M glycine-HCl pH 2.4. The eluates were neutralised with 1 m tris and used to probe blots of L3 antigen from Tc, Ns and Cc.

500 ml volumes of gut contents from immune sheep were treated with 45% ammonium sulphate to recover antibody. After dialysis, these antibodies were used to probe blots of L3 antigen. Larvae were incubated for 2 h with mucus supernatant or mucus antibody eluted from Protein G-Sepharose, washed 3 times with TBS-Tw and reacted with FITC-RAS/IgG. After washing, larvae were examined by fluorescence microscopy.

Larvae were collected from sheep at various times after infection and were analysed by immunofluorescence and immunoblotting as described above and by immunogold electron microscopy. Larvae were fixed in BGPA fixative (1% glutaraldehyde, 15% saturated picric acid in 0.1M phosphate buffer pH 7.2, at 90° C.). Embedded sections were stained with Protein G purified mucus antibody followed by gold labelled anti-sheep Ig.

Antibody titres of mucus samples used for in vivo challenge experiments were estimated by EIA. Microtitre plates were coated with Tc L3 antigen and reacted with dilutions of mucus. After washing, bound antibody was detected with RAS/IgG-HRP or mAb to sheep IgA (Serotek) followed by RAM/Ig-HRP.

1.7 Preparation of Monoclonal Antibody PAB-1

Mice were immunised with polyacrylamide gel slices containing the Tc larval surface antigen. The location of the antigen in the gel was determined by blotting adjacent lanes and detecting the antigen with mucus antibody as described. Antigen containing gel slices were macerated, mixed with an equal volume of an incomplete oil adjuvant and injected into mice on two occasions two weeks apart. Ten days later, test bleeds were taken and screened against crude Tc L3 antigen and partially purified surface antigen. Spleen cells from the strongest positive mouse were fused with NS-1 cells using standard methods for preparing monoclonal antibodies. Primary and secondary screening was performed using ELISA and blotting to confirm specificity. A bulk culture of mAb PAB-1 was prepared and aliquots stored at −20° C.

Monoclonal antibody PAB-1 was used to probe blots of larval antigens. Bound antibody was detected with RAM/IgG-HRP. Exsheathed larvae were fixed by heating at 90° C. for 20 minutes, reacted with PAB-1, washed extensively with TBS-Tw, reacted with RAM/IgG-FITC and examined under uv light. A mAb raised against an unrelated protein (sheep cytokine) and of the same subclass as PAB-1 was used as a negative control.

1.8 Immuno-affinity Purification of Larval Antigen

Monoclonal antibody PAB-1 was reacted with Protein A-agarose to allow the antibody to bind. After washing with PBS to remove unbound antibody, the bound antibody was permanently immobilised to the Protein A by reaction with the cross-linking agent DSS (disuccinimidyl suberate). After further washing, L3 extract was run through the PAB-1-Protein A-agarose column, washed extensively in PBS containing 0.05% Tween 20 and any bound antigen was eluted in 0.2 M glycine-HCl pH 2.5. The eluate was neutralised with 1 M Tris, dialysed against 5 mM Tris pH 8.0 and concentrated in a Speedvac concentrator. The antibody column was re-equilibrated by extensive washing with PBS.

Samples of the antigen eluted from the column were analysed by SDS PAGE and blotting (FIG. 23). Carbohydrate was detected in gels by staining with a modified silver strain (Kittelberger, et al, 1993) or on blots by reaction with biotin-hydrazide (Bouchez-Mahiout, et al, 1999).

1.9 Characterisation of Larval Antigen

Exsheathed Tc L3 were frozen in liquid $N_2$, ground with a mortar and pestle and proteins extracted by solubilisation in either 2% Chaps +2% Tween 20, 1% sodium deoxycholate (DOC), 2% SDS or 9 M urea. The extracts were centrifuged at 10 000 g and the supernatant stored at −20° C. Eggs, L1, L2 and adult nematodes were solubilised directly in SDS PAGE sample buffer (2% SDS, 20 mM DTT in 50 mM tris-HCl pH 6.8). SDS antigen extract was used for electrophoresis and blotting studies; Chaps and urea extract was used for 2D electrophoresis; urea extract was dialysed against 50 mM tris-HCl pH 7.4 for 2 days to remove urea prior to chemical or enzymatic treatments. Electrophoresis was also carried out using buffer only, 0.5% DOC or 6 M urea, with the appropriately solubilised antigen.

2D electrophoresis was performed by running Tc L3 urea extract on Immobiline IEF on pI 3-10 strips using the IPGphor (Pharmacia), followed by SDS PAGE. Proteins were either stained with Coomassie blue or silver, or reacted on blots with antibody from mucus to detect antigens. Tc L3 urea-solubilised antigen was dialysed as above and subjected to precipitation by addition of either an equal volume of 10% TCA; 10 volumes of cold acetone; 9 volumes of chloroform:methanol (2:1); or 9 volumes of hexane:isopropanol (3:2). Samples were vortexed and rocked for 10 min, centrifuged at 10000 g for 10 min and the precipitated pellets analysed by immunoblotting. The role of carbohydrates was investigated by chemical and enzymatic degradation. Antigen was treated with 20 mM periodic acid at 37° C. for 24 h; or with 1 M NaOH±8 M $NaBH_4$ for 18 h at 60° C. Samples were dialysed before electrophoresis. Antigen was treated with hydrazine for 7 and 14 days at 100° C., or with trifluoroacetic acid for 4 and 16 h at 4° C., after which the chemicals were evapourated using a Speedvac centrifuge and residual antigen was resolubilised in SDS PAGE sample buffer. Enzymatic digestions were carried out by dissolving each enzyme in the buffer recommended by the manufacturer and incubating with antigen for 22 h at 37° C. Enzymes used were N-glycosidase F, trypsin, pepsin, papain, pronase, proteinase K, subtilisin, lipase, lysozyme, elastase, collagenase, phosphoinositol-phospholipase C, phospholipase A2, phospholipase D. Coloured substrates casein-resorufin and elastin-Congo Red were used as controls for protease and elastase activity. In one experiment, antigen was heat denatured at 90° C. for 20 min prior to digestion with trypsin or NaOH. Proteinase K digestion was also performed at 50° C. for 18 h with or without 0.5% SDS, 15 mM DTT, 50 mM EDTA or 2 mM $CaCl_2$. Larval extracts of *Haemonchus contortus, Ostertagia circumcincta, Cooperia curticei* and *Nematodirus spathiger* were also treated with proteinase K under similar conditions.

1.10 Immunisation with the 35 kDa Antigen.

Five Romney sheep aged 12 months were injected i.p. on 3 occasions, 2 weeks apart, with 35 kDa antigen in a vegetable oil adjuvant containing Span 85, Tween 85 and sesame oil (ratio 5.4:4.6:90). The antigen was obtained from gel slices of electrophoretically separated Tc L3 antigen. After electrophoresis, the side strips of each gel were blotted to nitrocellulose and reacted with immune mucus to detect the 35 kDa antigen. After development with RAS/IgG-HRP, the blots were re-aligned with the main portion of the gel and a slice was excised corresponding to the location of the 35 kDa antigen. The gel slice was placed in dialysis tubing in 100 mM tris HCl pH 7.8 and the antigen was electroeluted from the gel by placing the dialysis tubing in a blotting tank at 50 v for 3 h. Multiple eluates were pooled and protein yield estimated to be 0.2 mg/ml by BCA protein assay. The antigen was blended with an equal volume of vegetable oil adjuvant using an Ultraturrax homogeniser. Each sheep received approximately 0.2 mg total protein at each injection although the amount of carbohydrate antigen was not known. Control sheep were injected i.p. with saline plus adjuvant. Two weeks after the third injection, all sheep were challenged infected orally with 40000 Tc L3. Faecal egg count data were obtained 3 and 4 weeks after challenge.

2. Results 2.1. In Vitro Assays

The ability of whole mucus or mucus subjected to various treatments to cause larval clumping in vitro is shown in Table 1 (refer page 33). The results indicate that dialysis or low speed centrifugation did not affect the ability of immune mucus to clump larvae. Centrifugation at 100 000×g reduced the larval clumping effect unless the detergents Tx-100 or CHAPS were present. Larval clumping activity was still present after heating at 60° C. for 5 min but not after heating at 100° C. Mucus treated with protease digestion or periodate oxidation lost activity but lipase treatment had no effect. The larval clumping activity was associated with the high molecular weight fraction of mucus.

2.2. In Vivo Assays

The effect of incubating L3 with increasing volumes of mucus, on subsequent displacement and reduction of numbers of larvae in naive recipient sheep is shown in FIG. 1. Larvae that were incubated in 5 or 10 ml of naive mucus were able to establish normally in the first 5 m of small intestine. Larvae that were incubated in immune mucus were progressively displaced or rejected as the volume of mucus was increased. Incubation of larvae with 10 ml immune mucus resulted in 82% reduction of larvae establishing and 100% displacement of larvae out of the first 5 m of intestine, compared to naive mucus.

The effect of incubating L3 with 10 ml volumes of mucus for different times is shown in FIG. 2. Incubation of immune mucus and L3 for as little as 1 h resulted in 46% reduction of larval establishment and 81% displacement from the first 5 m. Incubation for 4, 10 or 24 h resulted in >94% reduction and >93% displacement.

The effect on larval establishment of incubating L3 with 16 naive mucus samples and 25 immune mucus samples is shown in FIG. 3. Overall there was 67% reduction of larvae establishing in recipients of L3+immune mucus (range 0-95%) and there were 80% fewer larvae establishing in the first 5 m of intestine (P<0.001) of sheep given L3+immune mucus.

The influence of time of mucus collection on the anti-larval properties of mucus is shown in FIG. 4. Mucus collected 2-3 days after the last immunising dose of larvae was generally more active than mucus collected 1 week or later. Regression analysis showed a significant negative correlation between protection and time of mucus collection after immunisation.

The effect of incubating L3 with the 100 000×g supernatants of naïve or immune mucus, with or without subsequent washing, is shown in Table 2 (refer page 34). The result shows that L3 incubated in naïve mucus, supernatant or supernatant plus washing, were able to establish in naïve sheep. In contrast, L3 that had been incubated in immune mucus, supernatant or supernatant plus washing, were mostly prevented from establishing and there were 91% fewer L3 than in sheep receiving L3 treated with naïve mucus.

2.3 Mucus Biochemistry

Electrophoretic separation of mucus is shown in FIG. 5. The protein profiles of immune and naive mucus were highly complex and no clear cut differences were observed between the two sets of mucus. Lectin blotting also showed complex glycoprotein profiles for both sets of mucus (FIGS. 6, 7, 8) indicating that ranges of carbohydrate moieties were present. Again there was no clear difference in the binding of lectins to immune or naive mucus, with the exception of peanut agglutinin (FIG. 7A) where increased staining was seen with most of the immune samples at mw's of approximately 70 000 and 28 000 which may correspond to Ig heavy and light chains. However, when mucus was reacted with RAS/IgG-HRP, major bands were seen in all samples at 55 000 and 27 000, which probably correspond to IgG heavy and light chains (FIG. 8B).

2.4 Mucus Blotting

Immunoblots of TcL3 antigen probed with mucus or antibodies recovered from mucus are shown in FIG. 9. Six naive mucus samples (lanes 13-18) did not react with L3 antigen. Immune mucus samples reacted predominantly with a 35 kDa band as did antibody recovered by ammonium sulphate precipitation of gut contents from 2 immune sheep (lanes 8 and 9). Antibody from immune mucus supernatant purified on Protein G-agarose and antibody acid-eluted from L3 incubated with immune mucus also reacted with the 35 kDa band (lanes 4, 7 and 6, 20). Both IgG and IgA antibodies could be eluted off the L3 (FIG. 9, lanes 6 and 20). Serum from sheep given 3 truncated infections with Tc also contained antibodies that recognised the 35 kDa band plus many others (not shown). Antibody isotype specificity of the antibodies in mucus reacting with the 35 kDa band are shown in FIG. 10. $IgG_1$ and IgA isotype antibodies were present but $IgG_2$ or IgM antibodies were not detected.

Immunoblots of L3 antigen extracts from the intestinal parasitic nematodes *Nematodirus spathiger* (Ns) and *Cooperia curticei* (Cc) probed with mucus from Tc immune sheep showed predominant reactivity with bands at 22 kDa (FIG. 11, lanes 9 and 13). Serum from sheep given truncated infections of Ns reacted with these antigens in both Ns and Cc (lanes 12 and 16) and also with the 35 kDa band in Tc (lane8). Incubating 2 ml immune mucus with 260000 exsheathed Tc L3 resulted in complete depletion of antibody from the mucus (lane 1). Colloidal gold protein stain was used to detect proteins on the blot (lane 4). No staining was seen in the region corresponding to that detected by antibody from immune mucus (lanes 3 and 4). Extracts from L3 of the intestinal nematodes *N. spathiger* and *C. curticei* and the abomasal nematodes *H. contortus* and *O. circumcincta* were probed with Tc immune sheep mucus and showed reactions at 35 kDa for Tc and Hc; 39 kDa for Oc; 46 and 22 kDa for Cc; and 22 for Ns (FIG. 12). FIG. 33 shows blots of 1 M NaOH extracts of the intestinal nematodes *T. axei* (Ta), *T. vitrinus* (Tv), *O. ostertagi* (Ooi), *C. oncophera* (Co) and *D. eckerti* (De) and of the abomasal nematodes *H. contortus* (Hc) and *O. circumcincta* (Oc) the blots were probed with Tc immune sheep mucus and showed reactions at 35 kDa for Ta, Tv and Hc; 45, 35, 33 and 30 kDa for Oo; 45 and 20 kDa for Co; 12 and 9 kDa for Nb; and 30 kDa for De.

The correlation between mucus IgG and IgA antibody titres and the protection affforded by mucus used for in vivo challenges was analysed by linear regression (FIG. 13). There was a significant relationship between the titres of IgG and IgA antibodies against L3 antigen and protection (12=0.6; P<0.01). Antibody titres of mucus biopsy samples were high at day 3 after immunisation (FIG. 14) but both IgG and IgA titres fell away by 16 days but were still above background at 37 days after immunisation.

Immunofluorescent staining of larvae is shown in FIG. 15. Exsheathed L3 showed strong surface fluorescence after incubation with antibody from immune mucus but not with naive mucus (top panel). Larvae collected from sheep infected for 2, 3 or 4 days also showed surface staining (not shown) but at day 5 after infection, many larvae did not stain with antibody and some were observed in the process of moulting (lower panel). The shed L3 cuticle reacted with antibody from immune mucus but the emerging L4 did not stain. L4 collected at day 6 and 7 after infection also did not show surface staining.

Immunogold electron microscopy revealed a similar pattern of results where sections of L3 showed surface labelling with gold particles on the epicuticle (panel B, FIG. 16). Gold labelling was also observed on day 2 after infection, was weaker at day 3 and 4 and absent at day 5 (panels C, D, E and F, respectively).

Immunoblots of antigen extracts from eggs, L1, L2, L3 and from larvae collected at various times after infection were probed with mucus antibody (FIGS. 17 & 18). The 35 kDa antigen was seen in L3 before infection and up to 5 days after infection but was not present in the egg stage, L1 or L2, or in L4 at days 7 or 14 after infection, or in adult nematodes.

2.5 Monoclonal Antibody PAB-1

Comparative blotting reactions of mAb PAB-1 and Tc immune sheep mucus antibody against Tc L3 antigen are shown in FIG. 19. The mAb reacted with the main Tc L3 antigen at 35 kDa, a diffuse antigen at 35-40 kDa and a number of lower molecular weight antigens.

Identification of antigens in other nematode species is shown in FIG. 20. Extracts from L3 of the intestinal nematodes N. spathiger and C. curticei and the abomasal nematodes H. contortus and O. circumcincta were probed with mAb PAB-1 and showed reactions at approximately 35 kDa for Tc and Hc; 39 kDa for Oc; 46 and 22 kDa for Cc; and 22 for Ns (FIG. 20). After digestion of L3 extracts with proteinase K, immunoblotting against antibody from immune mucus or mAb PAB-1 showed that the larval antigens were not destroyed by this enzyme (FIGS. 19 and 20).

Reaction of mAb PAB-1 with exsheathed Tc L3 showed strong surface fluorescence after staining with anti-mouse FITC conjugate (FIG. 21). An $IgG_3$ control mAb did not react with the larval surface.

2.6 Immuno-affinity Purification of Larval Antigen

The results of immuno-affinity purification of larval antigen using the monoclonal antibody PAB-1 coupled to Protein A-agarose are shown in FIG. 22. Silver staining of the eluate showed that no protein-staining band was visible in the region where the larval antigen was expected to run. A single carbohydrate staining band was detected in the eluate which ran at the same molecular weight as the antigen detected by immunoblotting with antibody from immune sheep mucus. This band was also labelled in situ with biotin-hydrazide reagent which binds to exposed sugar residues after periodate oxidation.

2.7 Characterisation of Larval Antigen

The effect of various chemical and enzymatic treatments of L3 antigen on the immunoblot reaction of mucus antibody against the 35 kDa antigen is shown in FIGS. 23-30. Heating the antigen at 37° C. for 18 h had no effect on the immunoblot reaction to the 35 kDa antigen (FIG. 23, lane 2). Treatment with periodic acid or lipase slightly reduced the signal strength (FIG. 23, lanes 3, 5) but pronase had no effect (lane 4). The 35 kDa antigen was found in the precipitate after either acid or solvent precipitation (lanes 6-9).

Treatment of L3 antigen with trypsin, pepsin, proteinase K or phospholipase A2 caused the blot reaction to become more diffuse but did not reduce the molecular weight (FIG. 24, lanes 2, 3, 5, 11). Treatment with papain, subtilisin or lysing enzymes reduced the signal but did not alter the molecular weight (lanes 6-8). Pronase, lipase, lysozyme, phosphoinositol-phospholipase C and phospholipase D had no effect (lanes 4, 9, 10, 12, 13). Treatment with elastase resulted in the appearance of a slightly lower molecular weight band (FIG. 25, lane 1). Collagenase and proteinase K at 37° C. had no effect (lanes 2, 3, 4). Proteinase K treatment at 50° C. for 18 h under various conditions also did not destroy the 35 kDa antigen whichh could still be detected on blots (lanes 6-9). Treatment of L3 antigen with N-glycosidase F slightly reduced the blot signal but did not decrease the molecular weight of the 35 kDa antigen (FIG. 26, lane 4) under conditions where the control glycoprotein fetuin was degraded (lane 2) indicating that the enzyme was active. Treatment with 1 M NaOH at 60° C. for 18 h resulted in an increase in the number of lower molecular weight bands seen on the blot but the reaction at 35 kDa was still dominant (FIG. 27, lane 2). After treatment with NaOH plus $NaBH_4$, no protein was visible by silver staining although the blot reaction of the 35 kDa antigen was undiminished compared to the control antigen (FIG. 27, lane 3).

Treatment of L3 antigen with hydrofluorous acid for 48 h at 4° C. or with hydrazine for 1 h at 20° C. or for 16 h at 100° C., did not destroy the 35 kDa antigen (FIG. 28). Treatment with hydrazine for 7 or 14 days at 100° C. reduced the blot signal compared to untreated control antigen (FIG. 29, lanes 1, 2). Treatment with trifluoroacetic acid for 4 h or 16 h destroyed the antigen (FIG. 29, lanes 4, 5).

Treatment of L3 antigen by the following procedures did not destroy the 35 kDa antigen as shown by immunoblotting (FIG. 30): proteinase K+SDS for 4 h or 20 h at 50° C. (lanes 1 & 2): 0.1-1.0 M NaOH treatment at 37° C. for 18 h (FIG. 30, lanes 3,6,7,8): heat denaturation at 90° C. for 20 min prior to digestion with 1 M NaOH (lanes 4): trypsin digestion at 37° C. for 22 h with or without heat denaturation at 90° C. for 20 min (lanes 10 & 14): proteinase K+SDS+DTT at 50° C. for 22 h (lane 12). Proteinase K digestion of L3 extracts from five nematode species did not destroy the Tc 35 kDa antigen or the cross-reacting antigens of the other species present at 46, 35 or 22 kDa (FIG. 20).

Tc L3 extract was analysed by electrophoresis and blotting under native conditions and in the presence of 0.5% DOC or 6 M urea. The antigen ran as a high molecular weight smear under these conditions (FIG. 32). Addition of reducing agent (20 mM DTT) to the samples and the electrophoresis buffer did not alter these profiles (not shown).

2D electrophoretic analysis of Tc L3 urea extract showed a strong immunoblot reaction at 35 kDa, which extended across the range pH 3-10 (FIG. 33). Despite the strong blot signal, no protein was visible in the corresponding region.

3.6. Sheep Immunisation Trial

FEC data are shown in Table 3 (refer page 34). At week 3 after challenge, there was no significant difference in FEC between groups but at week 4, the counts were significantly lower in the immunised group (P<0.05). When counts from both weeks were combined, there was also a significant reduction of FEC overall in the immunised group(P<0.05).

FIG. 34 shows a Gel electrophoresis (8% PAGE) and immunoblot analysis of *T. colubriformis* L3 extract (L3) and purified carbohydrate larval antigen (C) run under non-denaturing conditions (no detergent or reducing agent). Gels were stained for protein or carbohydrate. Blots were reacted with mAb PAB-1 followed by rabbit anti-mouse Ig-HRP conjugate, or with immune sheep mucus followed by rabbit anti-sheep Ig-HRP conjugate.

TABLE 1

In vitro activity of immune mucus against L3 after various treatments

| Treatment | Larval clumping* |
|---|---|
| Untreated | +++ |
| Dialysis | +++ |
| 10000 × g supernatant | +++ |
| 50000 × g supernatant | ++ |
| 100000 × g supernatant | + |
| 100000 × g supernatant DTT | − |
| 100000 × g supernatant TX100 | ++ |
| 100000 × g supernatant CHAPS | ++ |
| Reduced and alkylated | ++ |
| Heated 60° C. | ++ |
| Heated 100° C. | − |
| Pepsin | + |
| Pronase | − |
| Periodate | − |
| Lipase | ++ |
| Retentate > 100000 mw | +++ |
| 10-100000 mw | − |
| 3-10000 mw | − |

*clumping score +++ = most larvae clumped together in large aggregates; ++ = some clumping; + = slight clumping; − = no clumping.

TABLE 2

Numbers of *T. colubriformis* larvae establishing in 5 m sections of small intestine of naïve sheep one week after infusion of L3 incubated with naïve or immune mucus, 100 000 × g mucus supernatant or supernatant followed by washing.

| Sample | 0-5 m | 5-10 m | 10-15 m | Total | % reduction* |
|---|---|---|---|---|---|
| Naïve mucus | 10664 | 140 | 0 | 10804 | |
| Supernatant | 24978 | 590 | 0 | 25568 | |
| Supernatant + wash | 8140 | 148 | 0 | 8288 | |
| Immune mucus | 148 | 770 | 0 | 918 | 91 |
| Supernatant | 130 | 0 | 396 | 526 | 98 |
| Supernatant + wash | 224 | 420 | 0 | 644 | 92 |

*% reduction in the numbers of larvae compared to respective naïve total.

TABLE 3

FEC data from sheep immunised with 35 kDa antigen

| Group | Individual FEC | mean | sd |
|---|---|---|---|
| Week 3 | | | |
| Controls | 600 700 1300 1500 1700 1800 2500 2500 | 1575 | 715 |
| Immunised | 300 400 800 1900 2400 | 1160 | 940 |
| Week 4 | | | |
| Controls | 900 1100 1300 1700 1800 2200 2500 4000 | 1938 | 993 |
| Immunised | 600 600 900 1100 1300 | 900 | 308* |

*significantly different to controls (P < 0.023, Kruskall-Wallis test).

3. Discussion

The ability of mucus from immune sheep to influence the survival of nematode larvae was indicated by earlier work where incubation of larvae with mucus caused inhibition of migration of larvae out of sieves (Douch et al 1983). Recently, we observed that larvae were frequently clumped together after incubation in immune mucus and that these larvae were prevented from establishing normally when infused into naive sheep via a duodenal cannula (Harrison et al 1999). These observations were extended in the present study and showed conclusively that immune mucus can effectively prevent establishment of larvae. The degree of protection against infection depended on the time of mucus collection after immunisation as well as dose volume. This correlates with the declining level of antibody in mucus over time as seen in mucus biopsy samples taken from truncated infection sheep up to 5 weeks after immunisation. The observation that the 100000×g supernatant of immune mucus could also prevent larval establishment indicates that this activity resides in the soluble fraction of mucus and does not result from physical blocking by mucus e.g. by viscosity. Washing the larvae after incubation did not affect the ability of immune mucus supernatant to prevent establishment, indicating that the activite factor was bound to the larvae.

In vitro analysis of larval clumping after treatment of immune mucus by dialysis, centrifugation or molecular weight filtration, indicated that the clumping activity was associated with the high molecular weight fraction of mucus. Heat treatment and protease digestion suggested that clumping required the protein component of mucus. However, SDS PAGE analysis and protein detection with Coomassie blue or silver staining did not reveal differences in the crude protein profiles of a panel of immune and naive mucus samples. Similarly, lectin blotting did not show differences in glycoprotein composition between the two panels of mucus, with the exception of peanut agglutinin, which may have detected carbohydrates present on heavy and light chains and seen in immune mucus samples. The heavy chains were at 70 kDa which could indicate the presence of IgA. Blotting also showed the presence of IgG in all mucus samples.

The above observations and presence of IgG and IgA in immune mucus suggested that antibodies recognising nematode antigens were responsible for larval clumping and for in vivo protection. Immunoblots of larval antigen probed with immune mucus showed the presence of $IgG_1$ and IgA antibodies which reacted predominantly with a major antigen at 35 kDa plus diffuse regions at 9, 12, 20, 3045 kDa. Significantly, blots of L3 antigens probed with antibodies eluted from intact exsheathed larvae after incubation in immune mucus also showed predominant reaction to this antigen. This result, plus the surface fluorescent staining and immunogold electron microscopy, show that the epitopes are present on the surface of the larvae. Anti-35 kDa antibody was present in mucus samples used for in vivo challenge experiments and there was a significant correlation between the degree of protection afforded by immune mucus and the titre of IgG and IgA. Mucus antibody from *T. colubriformis* immune sheep also recognised antigens on blots of larval extracts from other intestinal nematodes *C. curticei, N. spathiger, T. axei, T vitrinus, O. ostertagi, C. oncophora, N. brasiliensis* and *D. eckerti* and from abomasal nematodes *H. contortus* and *O. circumcincta*. This cross-reactivity indicates that a surface molecule with similar function to the *T. colubriformis* 35 kDa antigen exists in other nematode species and could be a target for immunisation. Monoclonal antibody PAB-1 also reacted with these antigens and could thus be used to identify and purify these surface antigens from parasitic nematode species. The finding that all the cross-reacting antigens tested so far are resistant to digestion by proteinase K is evidence that they are also not proteins and thus share similar properties to the *T. colubriformis* 35 kDa antigen.

Monoclonal antibody PAB-1 coupled to Protein A-agarose was able to purify *T. colubriformis* larval surface antigen. This *T. colubriformis* larval surface antigen was found to be predominantly carbohydrate as shown by its resistance to digestion with a range of proteases including proteinase K; by staining with a silver stain modified to detect carbohydrate groups and by labelling with a biotin-hydrazide reagent which binds to exposed sugar residues. The antigen did not stain with protein detecting methods such as silver stain, Coomassie blue or gold. The antigen was resistant to degradation by the action of lipases and was not soluble in organic solvents which suggests that lipid components are not present or not accessible. N-glycosidase F treatment did not affect the antigen indicating either that the sugars are not N-linked or that they are not accessible to enzyme attack. Alkali treatment or extensive hydrazinolysis did not destroy the antigen which may indicate an unusual carbohydrate structure. Strong acid hydrolysis with trifluoroacetic acid destroyed the antigen.

The observation of a multiple banding pattern in the form of a ladder of lower molecular weight antigens on blots of *T. colubriformis* larval extract probed with mAb PAB-1, could indicate that the structure of the 35 kDa antigen consists of a polymer of a smaller unit. In its native state on the larval surface, however, the antigen is a high molecular weight complex as shown by the electrophoresis results using non-denaturing conditions. Solubilisation in SDS+ DTT reduced the complex to an antigen detectable on blots at 35 kDa suggesting that the complex is a polymer of the 35 kDa antigen or a heteropolymer of 35 kDa antigen plus other components as yet unidentified. The antigen shows charge heterogeneity when separated by isoelectric focussing, again indicating a complex structure. The results suggest that this molecular complex, present on the outer surface of larvae, is likely to resist degradation by all physiological conditions found in the stomach and intestine of the nematode's host. The functional implications of these properties of the larval surface antigen have yet to be determined but it seems likely that this complex has evolved to protect the larva during transit through the hostile environment of the host system until it reaches it's site of predilection in the small intestine. The 35 kDa antigen was only found in the L3 before infection and up to 5 days after infection, suggesting that the coating was required for protection during transit through the stomach. During the moult to L4 stage in the small intestine, the protective coating is shed as it is no longer required. It will be appreciated that an immune response directed against this protective coat could severely compromise the nematode's ability to establish successfully in its host and could therefore have wide implications for nematode control. In a preliminary vaccine trial in sheep, immunisation with a vaccine containing partially purified 35 kDa antigen and an oil adjuvant resulted in a significant reduction of faecal egg count in the vaccinated group compared to controls.

Aspects of the present invention have been described by way of example only and it should be appreciated that modifications and additions may be made thereto without departing from the scope of the appended claims.

REFERENCES

Bouchez-Mahiout L., Doyen C., Lauriere M. 1999. Accurate detection of both glycoproteins and total proteins on blots: control of side reactions occurring after periodate oxidation of proteins. Electrophoresis: 20, 1412-1417.

Carlisle M S, McGregor D D, Appleton J A. Intestinal mucus entrapment of *Trichinella spiralis* larvae induced by specific antibodies. Immunology 1991; 74: 546-551.

Douch P G C, Harrison G B L, Buchanan L L, Greer K S. In vitro bioassay of sheep gastrointestinal mucus for nematode paralysing activity mediated by substances with some properties characteristic of SRS-A. Int J Parasitol 1983; 13:207-212.

Emery D L, McClure S J, Bendixsen T, Windon R G. Investigations of the role of hypersensitivity responses in immunity against ovine gastrointestinal nematodes. In: Husband A J, editor. Mucosal Solutions: Advances in Mucosal Immunology. University of Sydney Press, 1997; 359-366.

Harrison G B L, Pulford H D, Gatehouse T K, Shaw R J, Pfeffer A, Shoemaker C B. Studies on the role of mucus and mucosal hypersensitivity reactions during rejection of *Trichostrongylus colubriformis* from the intestine of immune sheep using an experimental challenge model. Int J Parasitol 1999; 29:459-468.

Jones W O, Windon R G, Steel J W, Outteridge P M. Histamine and leukotriene concentrations in duodenal tissue and mucus of lambs selected for high and low responsiveness to vaccination and challenge with *Trichostrongylus colubriformis*. Int J Parasitol 1990; 20:1075-1079.

Kittelberger R. and Hilbink F. 1993. Sensitve silver-staining detection of bacterial lipopolysaccharides in polyacrylamide gels. J. Biochem. Biophys. Methods 26: 81-6

Kohler and Milstein, Nature, 256, 495-497 (1975).

Lee G B, Ogilvie B M. The mucus layer in intestinal nematode infections. In: Ogra P L and Bienenstock J, editors. The Mucosal Immune System in Health and Disease. Columbus:Ross Laboratories 1981; 175-183.

Miller H R P. Gastrointestinal mucus, a medium for survival and for elimination of parasitic nematodes and protozoa. Parasitology 1987; 94:S77-S 100.

Miller H R P. Mucosal mast cells and the allergic response against nematode parasites. Vet Immunol Immunopathol 1996; 54:331-336.

Rothwell T L W. Immune expulsion of parasitic nematodes from the alimentary tract. Int J Parasitol 1989; 19:139-168.

Sangster and Gill, Pharmacology of Anthelmintic Resistance Parasitology Today. 1999, Vol 15, No. 4

Van Wyk, Stenson, Van Der Merwe, Vorster, Viljoen. Anthelmintic Resistence in South Africa: Surveys indicate an extremely serious situation in sheep and goat farming. 1999.

Waller, Anthelmintic Resistance. Veterinary Parasitology, 1997, 391-412.

The invention claimed is:

1. An isolated monoclonal antibody mAb PAB-1, deposited at ATCC on 24 Jan. 2002 and accorded accession PTA-4005, which binds to a surface antigen on nematode L3.

2. An isolated monoclonal antibody which binds to the following surface antigens isolated from stage L3 nematodes:
   a) a surface antigen on *C. curticei* which runs at substantially 46 kDa and at substantially 22 kDa on SDS PAGE gel under reducing conditions;
   b) a surface antigen on *N. spathiger* which runs at substantially 22 kDa on SDS PAGE gel under reducing conditions;
   c) a surface antigen on *H. contortus* which runs at substantially 35 kDa on SDS PAGE gel under reducing conditions; and
   d) a surface antigen on *O. circumcincta* which runs at substantially 35-39 kDa on SDS PAGE gel under reducing conditions;
   e) a surface antigen on *T. axei* or *T. vitrinus* which runs at substantially 35 kDa on SDS PAGE gel under reducing conditions;
   f) a surface antigen on *O. ostertagi* which runs at substantially 30-45 kDa on SDS PAGE gel under reducing conditions;
   g) a surface antigen on *C. oncophera* which runs at substantially 20 kDa and at substantially 45 kDa on SDS PAGE gel under reducing conditions;
   h) a surface antigen on *N. brasiliensis* which runs at substantially 9 kDa and at substantially 12 kDa on SDS PAGE gel under reducing conditions;
   i) a surface antigen on *D. eckerti* which runs at substantially 30 kDa on SDS PAGE gel under reducing conditions; and
   j) a surface antigen on *T. colubriformis* which runs at substantially 35 kDa on SDS PAGE gel under reducing conditions.

3. The isolated monoclonal antibody of claim 2, coupled to a solid support.

4. An isolated carbohydrate surface antigen from a nematode stage L3, comprising an antigen which binds to monoclonal antibody mAb PAB1, deposited at ATCC on 24 Jan. 2002 and accorded accession PTA-4005.

5. The isolated antigen of claim 4 wherein the antigen runs at about 20-35 kDa or at about 9 kDa and 12 kDa on SDS PAGE gel under reducing conditions.

6. The isolated antigen of claim 4 wherein the antigen is isolated from *T. colubriformis* stage L3.

7. The isolated antigen of claim 4 wherein the antigen is isolated from a nematode stage L3 selected from the group consisting of *C. curticei, N. spathiger, H. contortus, O. circumcincta, T. axei, T. vitrinus, O. ostertagi, C. oncophera, N. brasiliensis* and *D. eckerti*.

8. A composition that comprises an antigen as claimed in claim 4 together with a pharmaceutically or veterinarily acceptable carrier or diluent.

9. A method for treating, reducing the susceptibility to and/or reducing the establishment of nematode infection in a patient, comprising: administering an antigen according to claim 4.

10. A method for treating, reducing the susceptibility to and/or reducing establishment of nematode infection in susceptible sheep from nematodes selected from the group consisting of *T. colubriformis, C. curticei, N. spathiger, H. contortus, O. circumcincta T. axei, T. vitrinus, O. ostertagi, C. oncophera, N. brasiliensis* and *D. eckerti* comprising, administering an antigen according to claim 4.

11. The composition of claim 8 for treating, reducing the susceptibility to and/or reducing establishment of nematode infestation in susceptible animals other than sheep wherein these other species of nematodes also possess a larval surface antigen identified by reaction with monoclonal antibody PAB-1 as described above.

12. The composition of claim 8 further comprising at least one adjuvant or cytokine.

13. A method of diagnosing nematode infection in susceptible animals comprising the steps of:
   a) obtaining a blood sample from an animal; and
   b) identifying the presence of an antigen using the antibody of claim 2.

14. An isolated antibody which binds to the following surface antigens isolated from stage L3 nematodes:
   a) a surface antigen on *C. curticei* which runs at about 46 kDa and at about 22 kDa on SDS PAGE gel under reducing conditions;
   b) a surface antigen on *N. spathiger* which runs at about 22 kDa on SDS PAGE gel under reducing conditions;
   c) a surface antigen on *H. contortus* which runs at about 35 kDa on SDS PAGE gel under reducing conditions; and
   d) a surface antigen on *O. circumcincta* which runs at about 35-39 kDa on SDS PAGE gel under reducing conditions;
   e) a surface antigen on *T. axei* or *T. vitrinus* which runs at about 35 kDa on SDS PAGE gel under reducing conditions;
   f) a surface antigen on *O. ostertagi* which runs at about 30-45 kDa on SDS PAGE gel under reducing conditions,
   g) a surface antigen on *C. oncophera* which runs at about 20 kDa and at about 45 kDa on SDS PAGE gel under reducing conditions;
   h) a surface antigen on *N. brasiliensis* which runs at about 9 kDA and at about 12 kDa on SDS PAGE gel under reducing conditions;
   i) a surface antigen on *D. eckerti* which runs at about 30 kDa on SDS PAGE gel under reducing conditions; and
   j) a surface antigen on *T. colubriformis* which runs at about 35 kDa on SDS PAGE gel under reducing conditions,
wherein the antibody has been sourced from the gastrointestinal mucus of an animal which has been immunised by truncated infections with nematodes selected from the group consisting of *T. colubriformis, C. curticei, N. spathiger, H. contortus, O. circumcincta T. axei, T. vitrinus, O. ostertagi, C. oncophera, N. brasiliensis* and *D. eckerti*.

15. A method of treating, reducing susceptibility to and/or reducing establishment of animal nematode infections, comprising administering the composition of claim 8 to the animal.

16. A method to elicit an antibody response in the gut mucus of sheep or other susceptible animals to nematode infections, comprising administering the antigen of claim 4 to said sheep or other susceptible animals in an amount effective to elicit an antibody response in the gut mucus.

17. A method to detect nematode infection in sheep, comprising,
   a) obtaining a blood sample from an animal; and
   b) identifying the presence of an antibody against a nematode L3 antigen by adding the antigen of claim 4.

* * * * *

UNITED STATES PATENT AND TRADEMARK OFFICE
CERTIFICATE OF CORRECTION

| | | |
|---|---|---|
| PATENT NO. | : 7,326,774 B2 | |
| APPLICATION NO. | : 10/503456 | |
| DATED | : February 5, 2008 | |
| INVENTOR(S) | : Gavin Bernard Lear Harrison | |

It is certified that error appears in the above-identified patent and that said Letters Patent is hereby corrected as shown below:

At column 21, after "The invention claimed is:" please delete lines 2-40 encompassing:

"1. An isolated monoclonal antibody mAb PAB-1, deposited at ATCC on 24 January 2002 and accorded accession PTA-4005, which binds to a surface antigen on nematode L3.

2. An isolated monoclonal antibody which binds to the following surface antigens isolated from stage L3 nematodes:

a)     a surface antigen on *C. curticei* which runs at substantially 46 kDa and at substantially 22kDa on SDS PAGE gel under reducing conditions;

b)     a surface antigen on *N. spathiger* which runs at substantially 22kDa on SDS PAGE gel under reducing conditions;

c)     a surface antigen on *H. contortus* which runs at substantially 35kDa on SDS PAGE gel under reducing conditions; and d)     a surface antigen on *O. circumcincta* which runs at substantially 35-39kDa on SDS PAGE gel under reducing conditions;

e)     a surface antigen on *T. axei* or *T. vitrinus* which runs at substantially 35kDa on SDS PAGE gel under reducing conditions;

f)     a surface antigen on *O. ostertagi* which runs at substantially 30-45 kDa on SDS PAGE gel under reducing conditions;

g)     a surface antigen on *C. oncophera* which runs at substantially 20 kDa and at substantially 45 kDa on SDS PAGE gel under reducing conditions;

UNITED STATES PATENT AND TRADEMARK OFFICE
CERTIFICATE OF CORRECTION

| | | |
|---|---|---|
| PATENT NO. | : 7,326,774 B2 | |
| APPLICATION NO. | : 10/503456 | |
| DATED | : February 5, 2008 | |
| INVENTOR(S) | : Gavin Bernard Lear Harrison | |

It is certified that error appears in the above-identified patent and that said Letters Patent is hereby corrected as shown below:

h)     a surface antigen on *N. brasiliensis* which runs at substantially 9 kDa and at substantially 12 kDa on SDS PAGE gel under reducing conditions;

i)     a surface antigen on *D. eckerti* which runs at substantially 30 kDa on SDS PAGE gel under reducing conditions; and j)     a surface antigen on *T. colubriformis* which runs at substantially 35kDa on SDS PAGE gel under reducing conditions.

3. The isolated monoclonal antibody of Claim 2, coupled to a solid support."

At column 21, line 41, please delete "4" and insert therefore, --1--.

At column 21, line 45, please delete "5" and insert therefore, --2--.

At column 21, line 45, please delete "claim 4" and insert therefore, --claim 1--.

At column 21, line 48, please delete "6" and insert therefore, --3--.

At column 21, line 48, please delete "claim 4" and insert therefore, --claim 1--.

At column 21, line 50, please delete "7" and insert therefore, --4--.

At column 21, line 50, please delete "claim 4" and insert therefore, --claim 1--.

At column 21, line 55, please delete "8" and insert therefore, --5--.

At column 21, line 56, please delete "claim 4" and insert therefore, --claim 1--.

At column 21, line 58, please delete "9" and insert therefore, --6--.

At column 21, line 61, please delete "claim 4" and insert therefore, --claim 1--.

At column 21, line 62, please delete "10" and insert therefore, --7--.

At column 22, line 2, please delete "claim 4" and insert therefore, --claim 1--.

At column 22, line 3, please delete "11" and insert therefore, --8--.

UNITED STATES PATENT AND TRADEMARK OFFICE
CERTIFICATE OF CORRECTION

| | | |
|---|---|---|
| PATENT NO. | : 7,326,774 B2 | |
| APPLICATION NO. | : 10/503456 | |
| DATED | : February 5, 2008 | |
| INVENTOR(S) | : Gavin Bernard Lear Harrison | |

It is certified that error appears in the above-identified patent and that said Letters Patent is hereby corrected as shown below:

At column 22, line 3, please delete "claim 8" and insert therefore, --claim 5--.

At column 22, line 9, please delete "12" and insert therefore, --9--.

At column 22, line 9, please delete "claim 8" and insert therefore, --claim 5--.

At column 22, please delete lines 11-51 encompassing:

"13. A method of diagnosing nematode infection in susceptible animals comprising the steps of:

a)      obtaining a blood sample from an animal; and b)      identifying the presence of an antigen using the antibody of claim 2.

14. An isolated antibody which binds to the following surface antigens isolated from stage L3 nematodes:

a)      a surface antigen on *C. curticei* which runs at about 46 kDa and at substantially 22kDa on SDS PAGE gel under reducing conditions;

b)      a surface antigen on *N. spathiger* which runs at about 22kDa on SDS PAGE gel under reducing conditions;

c)      a surface antigen on *H. contortus* which runs at about 35kDa on SDS PAGE gel under reducing conditions; and d)      a surface antigen on *O. circumcincta* which runs at about 35-39kDa on SDS PAGE gel under reducing conditions;

e)      a surface antigen on *T. axei* or *T. vitrinus* which runs at about 35kDa on SDS PAGE gel under reducing conditions;

UNITED STATES PATENT AND TRADEMARK OFFICE
CERTIFICATE OF CORRECTION

PATENT NO. : 7,326,774 B2
APPLICATION NO. : 10/503456
DATED : February 5, 2008
INVENTOR(S) : Gavin Bernard Lear Harrison It is certified that error appears in the above-identified patent and that said Letters Patent is hereby corrected as shown below:

f) a surface antigen on *O. ostertagi* which runs at about 30-45 kDa on SDS PAGE gel under reducing conditions;

g) a surface antigen on *C. oncophera* which runs at about 20 kDa and at about 45 kDa on SDS PAGE gel under reducing conditions;

h) a surface antigen on *N. brasiliensis* which runs at about 9 kDa and at about 12 kDa on SDS PAGE gel under reducing conditions;

i) a surface antigen on *D. eckerti* which runs at about 30 kDa on SDS PAGE gel under reducing conditions; and j) a surface antigen on *T. colubriformis* which runs at about 35kDa on SDS PAGE gel under reducing conditions, wherein the antibody has been sourced from the gastrointestinal mucus of an animal which has been immunized by truncated infections with nematodes selected from the group consisting of *T. colubriformis, C. curticei, N. spathiger, H. contortus, O. circumcincta T. axei, T. vitrinus, O. ostertagi, C. oncophera, N. brasiliensis* and *D. eckerti.*"

At column 22, line 52, please delete "15" and insert therefore, --10--.

At column 22, line 54, please delete "claim 8" and insert therefore, --claim 5--.

At column 22, line 56, please delete "16" and insert therefore, --11--.

At column 22, line 58, please delete "claim 4" and insert therefore, --claim 1--.

UNITED STATES PATENT AND TRADEMARK OFFICE
CERTIFICATE OF CORRECTION

PATENT NO. : 7,326,774 B2
APPLICATION NO. : 10/503456
DATED : February 5, 2008
INVENTOR(S) : Gavin Bernard Lear Harrison It is certified that error appears in the above-identified patent and that said Letters Patent is hereby corrected as shown below:

At column 22, line 61, please "17" and insert therefore, --12--.

At column 22, line 65, please "claim 4" and insert therefore, --claim 1--.

Signed and Sealed this

Twenty-seventh Day of May, 2008

JON W. DUDAS
*Director of the United States Patent and Trademark Office*